US008962573B2

(12) United States Patent
Garcia et al.

(10) Patent No.: US 8,962,573 B2
(45) Date of Patent: Feb. 24, 2015

(54) COMPOUNDS TARGETING THE CATION-INDEPENDENT MANNOSE 6-PHOSPHATE RECEPTOR

(75) Inventors: Marcel Garcia, Montpellier Cedex (FR); Alain Morere, Montpellier (FR); Magali Gary-Bobo, Montpellier Cedex (FR); Martine Cerutti, Saint Christol les Ales (FR); Khaled El Cheikh, Montpellier Cedex (FR); Ilaria Basile, Montpellier Cedex (FR); Philippe Nirde, Montpellier Cedex (FR)

(73) Assignees: INSERM (Institut National de la Sante et de la Recherche Medicale), Paris (FR); Centre National de la Recherche Scientifique—CNRS, Paris (FR); Universite de Montpellier 1, Montpellier (FR); Universite de Montpellier 2 Sciences et Techniques, Montpellier (FR)

( * ) Notice: Subject to any disclaimer, the term of this patent is extended or adjusted under 35 U.S.C. 154(b) by 397 days.

(21) Appl. No.: 13/380,199

(22) PCT Filed: Jul. 2, 2010

(86) PCT No.: PCT/EP2010/059507

§ 371 (c)(1), (2), (4) Date: Dec. 22, 2011

(87) PCT Pub. No.: WO2011/000958

PCT Pub. Date: Jan. 6, 2011

(65) Prior Publication Data

US 2012/0093795 A1 Apr. 19, 2012

(30) Foreign Application Priority Data

Jul. 3, 2009 (EP) .................................... 09305647

(51) Int. Cl.

| | |
|---|---|
| ***C07G 3/00*** | (2006.01) |
| ***C07G 11/00*** | (2006.01) |
| ***C07H 15/00*** | (2006.01) |
| ***C07H 17/00*** | (2006.01) |
| ***A01N 43/04*** | (2006.01) |
| ***A61K 31/70*** | (2006.01) |
| ***A61K 47/48*** | (2006.01) |

(52) U.S. Cl.
CPC ............................... *A61K 47/48092* (2013.01)
USPC ................. 514/24; 514/25; 536/4.1; 536/124

(58) Field of Classification Search
CPC ............................................... A61K 47/48092
See application file for complete search history.

(56) References Cited

U.S. PATENT DOCUMENTS

| | | | |
|---|---|---|---|
| 7,001,994 | B2 | 2/2006 | Zhu |
| 7,365,178 | B2 | 4/2008 | Campbell et al. |
| 2010/0047225 | A1 | 2/2010 | Zhu et al. |

FOREIGN PATENT DOCUMENTS

| | | |
|---|---|---|
| EP | 1495769 | 1/2005 |
| JP | 2008-195757 | 8/2008 |
| WO | 00/23113 | 4/2000 |
| WO | 2005/049005 | 6/2005 |
| WO | 2006/002382 | 1/2006 |
| WO | 2008/089339 | 7/2008 |
| WO | 2008/125615 | 10/2008 |
| WO | 2009/024977 | 2/2009 |

OTHER PUBLICATIONS

Barragan et al., "A mannose-6-phosphonate-cholesterylamine conjugate as a specific molecular adhesive linking cancer cells with vesicles," Chem. Commun., pp. 85-86 (2001) XP002301443.

Brevet et al., "Mannose-targeted mesoporous silica nanoparticles for photodynamic therapy," Chem. Commun., 12:1475-1477 (2009) XP002607737.

Gary-Bobo et al., "Mannose 6-phosphate receptor targeting and its applications in human diseases," Curr. Med. Chem., 14(28):2945-2953 (2007) XP002557212.

Hamdaoui et al., "Synthese, etude structural et proprieties biologiques de bioconjugues de la pepstatine et du mannose-6-phosphate," Bulletin de la Societe Chimique de France, 131(8):854-864 (1994) XP001005269.

International Search Report and Written Opinion in PCT/EP2010/059507, dated Nov. 10, 2010.

Jeanjean et al., "Synthesis and receptor binding affinity of carboxylate analogues of the mannose 6-phosphate recognition marker," Bioorg. Med. Chem., 14(10):3575-3582 (2006) XP025133254.

Vidil et al., "Synthesis and Biological Activity of Phosphonate Analogs of Mannose 6-Phosphate (M6P)," Eur. J. Org. Chem., pp. 447-450 (1999) XP002607738.

(Continued)

*Primary Examiner* — Lawrence E Crane

(74) *Attorney, Agent, or Firm* — McAndrews, Held & Malloy Ltd.

(57) ABSTRACT

The invention relates to conjugates of products of interest including glycoproteins, nanoparticles, and imaging agents and of compounds of the general formula (1):

(1)

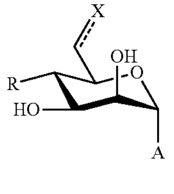

that target the cation-independent mannose 6-phosphate receptor with a high affinity. The invention also relates to their applications, for instance in enzyme replacement therapies.

18 Claims, 18 Drawing Sheets

(56) References Cited

OTHER PUBLICATIONS

Jeanjean et al., "Synthesis of new sulfonate and phosphonate derivatives for cation-independent mannose 6-phosphate receptor targeting," Bioorg. Med. Chem. Lett., 18:6240-6243 (2008).

Rachmawati et al., "Chemical Modification of Interleukin-10 with Mannose 6-Phosphate Groups Yields a Liver-Selective Cytokine," Drug Metab. Disposition, 35(5):814-821 (2007).

Luk et al., "Hepatic stellate cell-targeted delivery of M6P-HSA-glycyrrhetinic acid attenuates hepatic fibrogenesis in a bile duct ligation rat model," Liver Int., pp. 548-557 (2007).

Mannose 6-Phosphate (M6P) $IC_{50}$=2.3 $10^{-5}$ M

M6-Phosphonate 1 isosteric $IC_{50}$=1.3 $10^{-5}$ M

M6-Phosphonate 2 non isoteric $IC_{50}$>$10^{-2}$ M

Mannose 6-Malonate 3 $IC_{50}$=1.2 $10^{-5}$ M

Carboxylate analogue 4 $IC_{50}$ =7.4 $10^{-5}$ M

A

B saturated isostere OMe

A. $IC_{50}$=7.4 $10^{-5}$ M saturated isostere $OPhNH_2$

B. $IC_{50}$=4.4 $10^{-5}$ M

C. $IC_{50}$=3.6 $10^{-5}$ M ± 1.4 $10^{-5}$ M

Phosphonates AMFA-1-4

AMFA-1 hexanehydrazide spacer arm

AMFA-2 triazole-containing spacer arm

AMFA-3 2-(aminoxy)ethyl spacer arm

Phosphate

M6P-hexanehydrazide hexanehydrazide spacer arm

Malonate AMFA-5

AMFA-5 hexanehydrazide spacer arm mannose pentaacetate

1

2

3

4

5

6

7

8

9 (AMFA-1)

propargyl α-D-mannopyranoside

10

11

12

13

14

15

16 (AMFA-2)

2-bromoethyl α-D-mannopyranoside

17

18

19

20

21

22

23

24 (AMFA 3)

4

35

36

37

38

39 (AMFA-5)

4 32 33 34

| | IC50 | Stability (%) |
|---|---|---|
| AMFA-1 | $1.3.10^{-5}$ M ± $0.5.10^{-5}$ M | 85 |
| AMFA-2 | $3.8.10^{-5}$ M ± $1.6.10^{-5}$ M | 90 |
| AMFA-3 | $4.9.10^{-5}$ M ± $2.10^{-5}$ M | 91 |
| AMFA-5 | $1.4.10^{-4}$ M ± $0.7.10^{-4}$ M | 90 |
| M6P | $2.3.10^{-5}$ M ± $1.9.10^{-5}$ M | 0 |
| M6P-hexanehydrazide | $1.10^{-4}$ M ± $1.4.10^{-4}$ M | 16 |

COMPOUNDS TARGETING THE CATION-INDEPENDENT MANNOSE 6-PHOSPHATE RECEPTOR

The present application is filed pursuant to 35 U.S.C. 371 as a U.S. National Phase application of International Patent Application No. PCT/EP2010/059507, which was filed Jul. 2, 2010, claiming the benefit of priority to European Patent Application No. 09305647.1, which was filed on Jul. 3, 2009. The entire text of the aforementioned applications is incorporated herein by reference in its entirety.

FIELD OF THE INVENTION

The invention relates to compounds targeting the cation-independent mannose 6-phosphate receptor.

BACKGROUND OF THE INVENTION

The cation-independent mannose 6-phosphate receptor (CI-M6PR), a transmembrane glycoprotein of 300 kDa, plays very important roles in many biological processes. The main role of CI-M6PR is transporting and sorting those lysosomal enzymes that contain the mannose 6-phosphate (M6P) recognition marker in their structure from the trans-Golgi network to the lysosomes. CI-M6PR also mediates the endocytosis of extracellular M6P-containing ligands. The M6P-containing proteins, which differ from lysosomal enzymes and are internalized through CI-M6PR transport, include Granzyme B, a protease involved in cytotoxic-T-cell-induced apoptosis; the herpes simplex virus (HSV)[7]; and even leukemia inhibitory factor (LIF), a multifunctional protein that plays an important role in neuronal, platelet and bone formation. Renin is also internalized by CI-M6PR, which permits its clearance. CI-M6PR also acts on molecules that do not penetrate into cells such as the latent precursor of transforming growth factor-beta (L-TGFβ), the proform of a hormone that regulates cell growth, and acts in another process involved in L-TGFβ activation, the plasminogen/plasmin conversion by a serine protease, the urokinase-type plasminogen activator (uPA). The pro-uPA is proteolytically cleaved and thereby activated when bound at the cell surface to a specific uPA receptor (uPAR) that presents an affinity for CI-M6PR. Moreover, studies suggest that CI-M6PR may act as a tumour suppressor as it modulates the local level of mitogen insulin-like growth factor II (IGF2), and loss of CI-M6PR function is associated with the progression of a high proportion of hepatocarcinomas. As CI-M6PR binds and endocytoses IGF2 in order to decompose it into lysosomal compartments, this receptor is also called M6P/IGF2 receptor. Another ligand of this receptor is retinoic acid, which is involved in apoptosis and growth inhibition. These three ligands (M6P, IGF2, retinoic acid) are recognized by different extracellular binding sites located on CI-M6PR, which contains 15 repeat domains. The phosphate moiety as well as the hydroxyl groups on the mannopyranosidic ring of M6P contribute to a hydrogen-bonding network with two binding sites located on domains 3 and 9 of CI-M6PR. This ability to recognize two M6P residues allows CI-M6PR to bind lysosomal enzymes with high affinity (Kd=2 nM).

The use of this strong affinity between M6P and CI-M6PR has been proposed to develop enzyme replacement therapies, in particular for lysosomal enzymes deficiencies.

However, supplies for the required enzymes are limited and large-scale production of sufficient quantities of enzymes for therapeutic administration is difficult. In addition, lysosomal enzymes purified from recombinant expression systems are often not well phosphorylated and the extent of M6P phosphorylation varies considerably with different enzymes. Lysosomal enzymes lacking in M6P phosphorylation compete poorly for receptor-mediated endocytic uptake by target cells and are thus of limited efficacy in enzyme replacement therapy.

Zhu (U.S. Pat. No. 7,001,994) proposes methods for introducing highly phosphorylated mannopyranosyl oligosaccharides containing M6P to carbonyl groups generated on the glycosidic part of lysosomal enzymes while retaining their biological activity. These mannopyranosyl oligosaccharides containing M6P are typically phosphopentamannose and are chemically treated to contain a carbonyl-reactive group in lieu of an hydroxyl group of the sugar bone. This carbonyl-reactive group is then reacted with an oxidized glycoprotein to form a M6P-glycoprotein. As shown in the experimental section of U.S. Pat. No. 7,001,994, these compounds, whereas conserving a good enzymatic activity, have a poor affinity for the CI-M6PR. According to Zhu, this low affinity is due to steric hindrance of the vicinal aldehyde groups.

These compounds are therefore not suitable for a satisfactory enzyme replacement therapy and there is thus a need for new compounds having a high affinity to the CI-M6PR (thereby allowing a specific addressing of the compounds to the lysosome) and conserving a good biological activity.

SUMMARY OF THE INVENTION

The invention relates to conjugates of products of interest and of compounds targeting the cation-independent mannose 6-phosphate receptor with a high affinity. These products of interests, for instance glycoproteins and nanoparticles, are therefore specifically addressed to the lysosome. The conjugates according to the invention therefore have numerous applications in the field of diagnostic and therapy, and particularly in enzyme replacement therapies for treating lysosomal storage disorders in the human or animal body.

DETAILED DESCRIPTION OF THE INVENTION

The invention relates to a conjugate, wherein said conjugate is

- product of interest Y selected from the group consisting of glycoproteins, nanoparticles and labels for medical imaging, conjugated via a linker L with
- a compound having the formula (1)

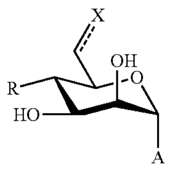

(1)

wherein

- the dotted line represents a bond which is present or not,
- X represents an analogue of a phosphate group,
- R is selected from the group consisting of H and OH,
- A is selected from the group consisting of O, S and $CH_2$, and wherein

- said compound having the formula (1) is linked to the linker via the A moiety,
- said linker L separates A and Y by a chain of 4 to 15 consecutive atoms, when said bond represented by the dotted line is not present, X is selected from the group consisting of:

a saturated phosphonate group having the formula (X₁)

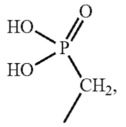

a bis-fluoro phosphonate group having the formula (X₂)

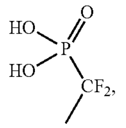

a fluoro phosphonate group having the formula (X₃)

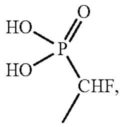

a saturated carboxylate group having the formula (X₄)

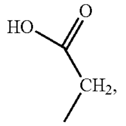

and a malonate group having the formula (X₅)

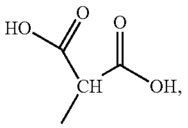

when said bond represented by the dated dotted line is present, X is selected from the group consisting of:

an unsaturated phosphonate group having the formula (X₆)

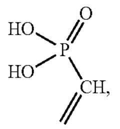

and an unsaturated carboxylate group having the formula (X₇)

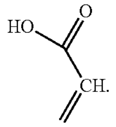

As used herein, a "conjugate" refers to two products/compounds covalently linked together.

As used herein, "to conjugate" means to link two products/compounds together.

As used herein, "M6P" means mannose 6-phosphate.

As used herein, "CI-M6PR" means cation-independent mannose 6-phosphate receptor.

According to the invention, the number of "consecutive atoms" has to be calculated from the first atom of the linker to the last atom of the linker following the shorter chain of consecutive atoms. Indeed, if the linker contains cyclic or heterocyclic systems, the number of atoms has to be calculated by following the shorter chain of atoms between A and Y.

An example of numeration according to the invention is given in the formula hereinafter:

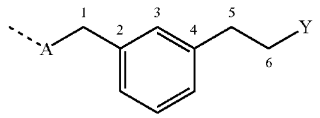

As shown in this formula, this linker separates A and Y by a chain of 6 consecutive atoms.

The conjugates according to the invention, which comprise a particular terminal M6P analogue, specifically target the CI-M6PR with a high affinity, never obtained to date.

In addition, during their research, the inventors have also shown that it is possible to increase the affinity of a product containing a terminal M6P analogue for the CI-M6PR by introducing a linker having a particular length between the M6P analogue and the product of interest which has to be addressed to the lysosome. Without wanting to be bound by a theory, the M6P-containing products known to date, such as for instance the products disclosed in U.S. Pat. No. 7,001,994, have a bad affinity for the CI-M6PR and thus poor addressing properties because of the steric hindrance induced by the product itself nearby the M6P binding sites of the CI-M6PR. Thanks to the linker according to the invention, the steric hindrance around the M6P binding sites of the CI-M6PR is reduced or cancelled (see FIG. 1 of the invention), therefore explaining the dramatic increase of the affinity of the conjugates according to the invention for the CI-M6PR compared to the products known in the prior art.

The conjugates of the invention thus represent very promising candidates for enzyme-replacement therapy of lysosomal diseases.

As mentioned previously, the conjugates according to the invention have a high affinity ($IC_{50}$) for the CI-M6PR. Particularly, the conjugates according to the invention have a minimal $IC_{50}$ of 100 μM, i.e. an $IC_{50}$ of at most 100 μM, as measured by the receptor binding assay described in Jeanjean A. et al., Bioorganic & Medicinal Chemistry, 14 (2006) 3575-3582.

According to the invention, any type of linker L ensuring a sufficient spacing between the M6P analogue moiety and the product which is linked to the compound according to the invention is suitable. The inventors have found that "sufficient spacing" between the M6P analogue moiety and the product is obtained when the linker separates A and Y by 4 5, 6, 7, 8, 9, 10, 11, 12, 13, 14 or 15 consecutive atoms This length of the linker has been found to allow an optimal penetration of the M6P analogue into the binding pocket of the CI-M6PR, thereby ensuring the maximal affinity of the compound according to the invention with the CI-M6PR.

According to the invention, the choice of the linker will depend on the nature of the product of interest to be conjugated with the compound of formula (1). Indeed, the skilled person easily understands that the length of the linker will increase with the steric hindrance associated with the product which is to be linked. For example, if the product is a protein that does not cause an important steric hindrance nearby the M6P binding sites of the CI-M6PR, a linker of 4 consecutive atoms is sufficient to ensure satisfactory affinity of the protein with the CI-M6PR. In contrast, if the product is a protein, a nanoparticle or any product of interest causing an important steric hindrance nearby the M6P binding sites of the CI-M6PR, a linker of more than 4 consecutive atoms will be necessary to ensure satisfactory affinity of the product with the CI-M6PR.

Typically, in the compounds according to the invention, said chain of atoms of said linker L is a substituted or not, linear or branched alkyl or alkenyl chain, particularly a substituted or not, linear or branched $C_1$-$C_{30}$ alkyl or alkenyl chain, wherein one or more carbon atom of said chain are optionally replaced by a chemical group selected from the group consisting of ether (—O—), amine (—NH), thioether (—S—), amide (—CO—NH—), urea (—NH—CO—NH—), carbamate (—NH—CO—O—), and cyclic or heterocyclic systems, said cyclic or heterocyclic systems being saturated or not and substituted or not, provided that said chain separates the A and the Y moieties by at least 4 consecutive atoms.

Typically, said $C_1$-$C_{30}$ alkyl or alkenyl chain according to the invention is a $C_1$-$C_{25}$ alkyl or alkenyl chain, particularly a $C_1$-$C_{20}$ alkyl or alkenyl chain, still particularly a $C_1$-$C_{15}$ alkyl or alkenyl chain. Said $C_1$-$C_{15}$ alkyl or alkenyl chain is typically a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ or $C_{15}$ alkyl or alkenyl chain.

In a particular embodiment, said cyclic or heterocyclic systems are selected from the group comprising azetidine, oxetane, thietane, pyrrole, pyranose, furanose, furan, pyrroline, tetrahydrofuran, thiophene, tetrahydrothiophene, pyrazole, imidazole, oxazole, isoxazole, pyrazoline, imidazoline, pyrazolidine, imidazolidine, dioxolane, thiazole, isothiazole, thiazolidine, isoxazolidine, triazole, oxadiazole, furazan, thiadiazole, tetrazole, pyridine, naphthyridine, pyran, dihydro-pyran, piperidine, pyridazine, pyrimidine, purine, pyrazine, pteridine, oxazine, dioxine, piperazine, morpholine, dioxane, thiazine, thiomorpholine, oxathiane, dithiane, triazine, trioxane, thiadiazine, dithiazine, trithiane, cyclobutane, cylcobutene, cyclopentane, cyclopentene, cyclohexane, cyclohexene cycloheptane, cycloheptene, and benzene and its derivatives.

As previously mentioned, said alkyl or alkenyl chain and said cyclic or heterocyclic systems may be substituted, for instance by a $C_1$-$C_{10}$ alkyl (i.e. a $C_1$, $C_2$, $C_3$, $C_4$, $C_5$, $C_6$, $C_7$, $C_8$, $C_9$ or $C_{10}$ alkyl), such as for example by a methyl, ethyl, propyl or isopropyl, or by functional groups such as for examples by alcohol, amine, amide, ketone, ester, ether or acid functions, etc.

A particular example of a substituted cyclic system according to the invention is the cyclobut-3-ene-1,2-dione.

Examples of derivatives of benzene are indene, indane, indolizine, indole, benzofuran, indoline, benzothiophene, indazole, benzimidazole, benzthiazole, naphthalene, tetralin, quinoline, chromene, chromane, cinnoline, quinazoline, quinoxaline and phthalazine.

In a particular embodiment, the linker L according to the invention has a chemical structure selected from the group consisting of:

(L1)

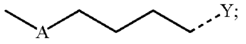

(L2)

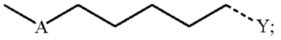

(L3)

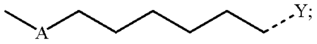

(L4)

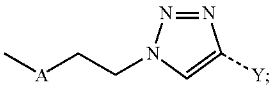

(L5)

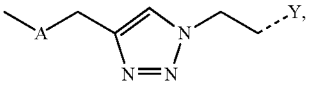 and (L6)

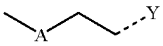

wherein

"-----Y" represents either:

(a) —Y, or (b) -T-Y, wherein T is part of the linker and represents a chemical moiety selected from the group consisting of

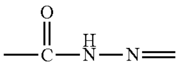 and —O—N═;

and

"A-" represents the remainder of the compound according to the invention as defined in formula (1).

In the conjugates according to the invention, Y is conjugated with at least one compound having formula (1). In a particular embodiment, in the conjugates according to the invention, Y is conjugated with more than one compound having formula (1). Typically, said product of interest Y is conjugated via a linker L according to the invention with at least 1, 2, 3, 4, 5, 6, 7, 8, 9, 10, 100, 1000 or more compounds having the formula (1) according to the invention. This number will depend on the nature of the product Y which is conjugated. For instance, if this product Y is a nanoparticle, said nanoparticle may be conjugated via a linker L according to the invention with more than 1000 compounds having the formula (1), in particular with 200 000 to 400 000 compounds having the formula (1).

According to the invention, when Y is conjugated with more than one compound of formula (1), each compound is linked to Y via a linker L which can be identical or different (in other words and for example, if Y is conjugated with 5 compounds having formula (1), each compound having formula (1) is conjugated to Y via a linker L, each linker L being identical or different).

In addition, since the CI-M6PR contains two binding sites for the M6P, the affinity of the conjugates according to the invention for the CI-M6PR will be better if both binding sites of said CI-M6PR are occupied by two M6P analogues of a same conjugate in an order of 50 to 100 fold. Similarly, when two CI-M6PRs are in dimeric form, the affinity of the conjugates according to the invention for the CI-M6PR dimer will be better if at least two binding sites of the four binding sites of said CI-M6PR dimer are occupied by the M6P analogues of the conjugate.

Accordingly, in one embodiment, the conjugate according to the invention is a product of interest Y conjugated via a linker L with at least two compounds having the formula (1), wherein two M6P analogues of said at least two compounds are recognizable by the two M6P binding sites of a same CI-M6PR or by two M6P binding sites of a CI-M6PR dimer. In still another embodiment, the conjugate according to the invention is a product of interest Y conjugated via a linker L with at least four compounds having the formula (1), wherein four M6P analogues of said at least four compounds are recognizable by the four M6P binding sites of a CI-M6PR dimer.

The skilled person is able to calculate the number of compounds having formula (1) which is necessary to conjugate with Y to obtain compounds with a high affinity for the CI-M6PR. As easily understandable by the skilled person, the probability of having two M6P analogues spatially arranged in a way allowing their recognition by two binding sites of a same CI-M6PR or by two binding sites of a CI-M6PR dimer will increase with the number of compounds having formula (1) which are linked to the compound Y. The higher the number of compounds having formula (1) conjugated with Y is, the higher the probability of having a conjugate with a high affinity for the CI-M6PR is. According to the selected Y structure, the skilled person is able to calculate the optimal concentrations of compounds of formula (1) to reach high affinity for the CI-M6PR and avoiding steric hindrance due to the close proximity between compounds of formula (1).

Hence, the affinity of the conjugates according to the invention will typically increase with the number of compounds having formula (1) conjugated with Y. Accordingly, when two M6P analogues of at least two compounds of the conjugate are recognizable by the two M6P binding sites of a same CI-M6PR, or when two M6P analogues of at least two compounds of the conjugate are recognizable by two M6P binding sites of a CI-M6PR dimer, or when four M6P analogues of at least four compounds of the conjugate are recognizable by the four M6P binding sites of a CI-M6PR dimer, then the conjugates according to the invention have an $IC_{50}$ of at most 100 nM, particularly of at most 50 nM, more particularly of at most 25 nM, most particularly of at most 2 nM.

In another embodiment, in said conjugates according to the invention, said compound of formula (1) has the formula (1) wherein the bond represented by the dotted line is not present, and X is a saturated phosphonate group having the formula $(X_1)$

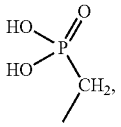

and

A is as defined previously.

In a particular embodiment, the invention relates to a conjugate, wherein said conjugate is

- a product of interest Y selected from the group consisting of glycoproteins, nanoparticles and labels for medical imaging, conjugated via a linker L with
- a compound having the formula (1)

(1)

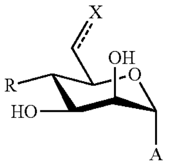

wherein

- the dotted line represents a bond which is present or not,
- when said bond is not present, X is selected from the group consisting of $X_1$, $X_2$, $X_3$, $X_4$, and $X_5$,
- when said bond is present, X is selected from the group consisting of $X_6$ and $X_7$,
- R is selected from the group consisting of H and OH,
- A is 0, and wherein

- said compound having the formula (1) is linked to the linker via the A moiety, and
- said linker L separates A and Y by a chain of 4 to 15 consecutive atoms, said linker L having or comprising a formula selected from the group consisting of $L_1$, $L_2$, $L_3$, $L_4$, $L_5$, and $L_6$.

In a particular embodiment, the invention relates to a conjugate, wherein said conjugate is

- a product of interest Y selected from the group consisting of glycoproteins, nanoparticles and labels for medical imaging, conjugated via a linker L with In a particular embodiment of the invention, the conjugates according the invention are selected from the group consisting of:

(2)

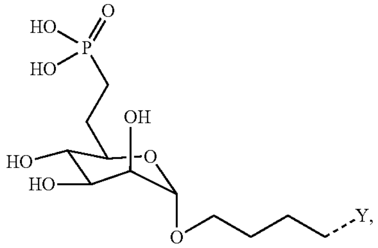

(3)

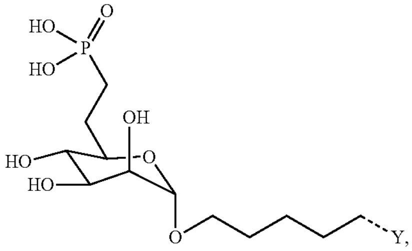

-continued (4)

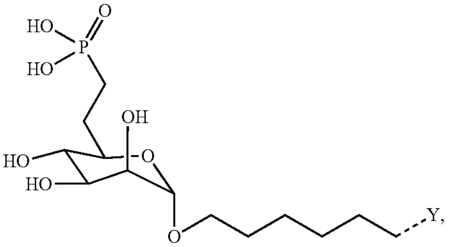

(5)

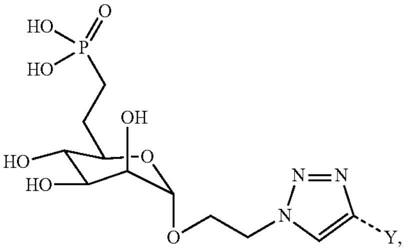

(6)

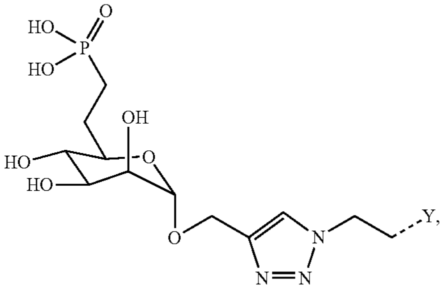

(7)

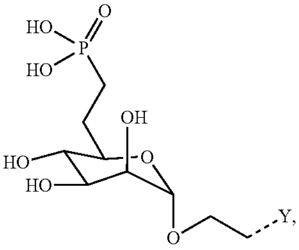 and (8)

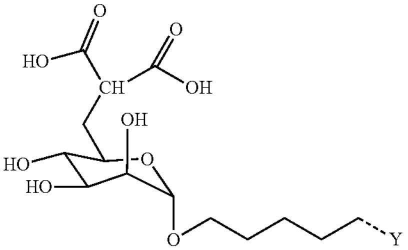

wherein "-----Y" represents either:

(a) —Y, or (b) -T-Y, wherein T is part of the linker and represents a chemical moiety selected from the group consisting of

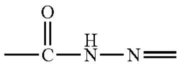 and .

The product of interest according to the invention is selected from the group consisting of glycoproteins, nanoparticles and labels for medical imaging (e.g. radiolabel, fluorescent label, etc.).

Nanoparticles can be of different natures: examples of nanoparticles are dendrimer nanoparticles, micelle nanoparticles, liposome nanoparticles, mesoporous silica nanoparticles and magnetic nanoparticles. These nanoparticles have various applications, for instance for drug delivery (therapeutic or cytotoxic drug), cancer therapy, magnetic resonance, fluorescence imaging, magnetic manipulation or cell targeting, as for instance described by Liong M. et al., ACS Nano. 2: 889-96, 2008.

In one embodiment, said product of interest Y is a glycoprotein.

Accordingly, in one embodiment, the invention relates to a conjugate, wherein said conjugate is a glycoprotein conjugated via a linker L according to the invention with a compound having the formula (1) according to the invention.

Typically, the glycoprotein is conjugated to a compound having formula (1) according to the invention via a linker L, said linker linking an oligosaccharide chain of said glycoprotein to the compound having formula (1). In other words, the analogue of M6P is conjugated to an oligosaccharide chain of the glycoprotein via the linker L.

Accordingly, in a particular embodiment, the invention relates to a conjugate, wherein said conjugate is a glycoprotein conjugated via a linker L according to the invention with at least two compounds having the formula (1) according to the invention, said compounds being linked to the same oligosaccharide chain or to two different oligosaccharide chains of said glycoprotein, and wherein two M6P analogues of said at least two compounds are recognizable by the two M6P binding sites of a same CI-M6PR or by two M6P binding sites of a CI-M6PR dimer.

In still another embodiment, the invention relates to a conjugate, wherein said conjugate is a glycoprotein conjugated via a linker L according to the invention with at least four compounds having the formula (1) according to the invention, said compounds being linked to the same oligosaccharide chain or to two different oligosaccharide chains of said glycoprotein, and wherein four M6P analogues of said at least two compounds are recognizable by the four M6P binding sites of a CI-M6PR dimer.

According to the invention, when said glycoprotein is conjugated with more than one compound of formula (1), each compound is linked to said glycoprotein via a linker L which can be identical or different.

Typically, the conjugate according to the invention, wherein Y is a glycoprotein, have a binding affinity for the CI-M6PR ($IC_{50}$) of at most 100 nM as measured by a method described in Jeanjean et al *Bioorg Med Chem* (2006) 14:3575-82. Particularly, said conjugates according to the invention have a binding affinity for the CI-M6PR ($IC_{50}$) of at most 50 nM. More particularly, said conjugates according to the invention have a binding affinity for the CI-M6PR ($IC_{50}$) of at most 25 nM. Most particularly, said conjugates according to the invention have a binding affinity for the CI-M6PR ($IC_{50}$) of at most 2 nM.

In one embodiment, said glycoproteins are lysosomal enzymes.

In a particular embodiment, said lysosomal enzymes are selected from the group comprising Acid beta-galactosidase-1, Acid sphingomyelinase, Alpha-D-mannosidase, Alpha-fucosidase, Alpha-galactosidase A, Alpha-glucosaminide acetyltransferase, Alpha-glucosidase, Alpha-L-iduronidase, Alpha-N-acetylgalactosaminidase, Alpha-n-acetylglucosaminidase, Alpha-neuraminidase, Arylsulfatase A, Arylsulfatase B, Beta-galactosidase, Beta-glucuronidase, Beta-mannosidase, Cathepsin D, Cathepsin K, Ceramidase, Cystinosin, Galactocerebrosidase, Glucocerebrosidase, GM2 ganglioside activator, Heparan sulfatase, Hexosaminidase A and Hexosaminidase B, Hyaluronidase, Iduronate sulfatase, LAMP2, Linclin, Lysosomal acid lipase, N-Acetylglucosamine-1-phosphotransferase, N-acetylgalactosamine 6-sulfatase, N-Acetylglucosamine-1-phosphotransferase, N-acetylglucosamine-6-sulfate sulfatase, N-aspartyl-beta-glucosaminidase, Palmitoyl-protein thioesterase-1, Protective Protein/Cathepsin A (PPCA), Sialin, TPP1 enzyme.

Typically, the glycoproteins to be linked to the compounds according to the invention are produced by genetic engineering with recombinant expression systems. Typically, said glycoproteins are produced with expression systems allowing the production of high levels (up to 1000 mg/L) of properly post-translationally modified (folding, disulfide bond formation, oligomerization, glycosylation, acylation, proteolytic cleavage), biologically active and functional recombinant proteins. A typical expression system according to the invention is the Baculovirus Expression Vector System. The Baculovirus Expression Vector System is based on the introduction of a foreign gene into a genome region nonessential for viral replication via homologous recombination with a transfer vector containing the target gene. The resulting recombinant Baculovirus lacks one of nonessential gene (e.g. polh, v-cath, chiA etc.) replaced with foreign gene encoding heterologous protein. Said protein, typically a glycoprotein, can be expressed in cultured insect cells and insect larvae. Typically, the expression of the glycoprotein is performed in insect cells, which lead to a satisfactory glycosylation of the proteins. More particularly, the expression is performed in cells of the cell line Sf9 (*Spodoptera frugiperda*), which allow a satisfactory glycosylation of the proteins, said glycosylation being free of α-1,3-fucose residues which are immunogenic for human.

Another object of the invention concerns the conjugate according to the invention, for use in a diagnostic method practised on the human or animal body. Indeed, since the conjugates according to the invention have a high affinity for the CI-M6PR, they can be useful in the diagnosis of diseases or conditions associated with an increase or decrease in the expression of CI-M6PR.

Another object of the invention concerns the conjugates according to the invention, for use in a method for treatment of the human or animal body. Indeed, the conjugates according to the invention have numerous applications in the field of medicine.

For instance, it has been shown that in some prostate cancers, CI-M6PRs are overexpressed and anti-CI-M6PR autoantibodies are released in the blood circulation (Huang Y Y, et al. Clinical Immunology 2004; 111 (2):202-9): by using a conjugate according to the invention comprising for instance a fluorescent label or a radiolabel, it is possible to identify the areas of the body where CI-M6PRs are overexpressed and consequently to irradiate the patient very precisely, only in the areas which need to be treated.

Other examples of diseases that can be treated with the conjugates according to the invention are the diseases caused by a deficiency in a product Y in the lysosome. This deficiency can be compensated by the administration of a conjugate according to the invention, which is capable to specifically deliver the deficient product Y to the lysosome.

The invention also particularly relates to the conjugate according to the invention, for use in a method for treatment of a lysosomal storage disorder in the human or animal body. Indeed, when Y is a lysosomal enzyme, the conjugates according to the invention can be used in methods for treatment of a lysosomal storage disorder wherein said lysosomal enzyme Y is missing or deficient.

The invention also relates to a method for treating a patient suffering from a lysosomal storage disorder, said method comprising the step of administering to said patient a therapeutically effective amount of a conjugate according to the invention wherein Y is a lysosomal enzyme missing or deficient in said lysosomal storage disorder.

As used herein, by “missing” it is meant that said lysosomal enzyme is not produced by the patient suffering from said lysosomal disease.

As used herein, by “deficient” it is meant that said lysosomal enzyme is produced by said patient suffering from said lysosomal disease in a quantity which is not sufficient or in an inactive form.

For each lysosomal storage disorder to be treated, the skilled person is able to select the appropriate lysosomal enzyme to be administered in order to treat said disease. Indeed, the molecular basis of lysosomal storage disorders is well known and for instance disclosed by Winchester B et al. in Biochem Soc Trans. 2000 February; 28(2):150-4.

Non limitative examples of lysosomal storage disorder which can be treated according to the invention are Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II and Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS IIIC, Sanfilippo syndrome Type D/MPS III D, Morquio Type A/MPS WA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, B, C), Neuronal Ceroid Lipofuscinoses (CLN6 disease—Atypical Late Infantile, Late Onset variant, Early Juvenile—, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, and Wolman disease.

In the context of the invention, the term “treating” or “treatment”, as used herein, means reversing, alleviating, inhibiting the progress of, or preventing the disorder or condition to which such term applies.

As used herein, "subject" or "patient" refers to a human or animal that may benefit from the administration of a product as recited herein.

By a "therapeutically effective amount" of a product as described previously, is meant a sufficient amount to treat the disease, at a reasonable benefit/risk ratio applicable to any medical treatment.

Another aspect of the invention relates to compounds having the formula (I)

(I)

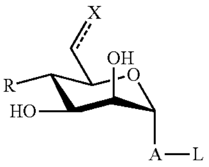

wherein the dotted line represents a bond which is present or not,

X represents an analogue of a phosphate group,

R is selected from the group consisting of H and OH,

A is selected from the group consisting of O, S, and $CH_2$,

L represents a linker comprising a terminal chemical reactive group Z capable of reacting with a product of interest Y to form a conjugate wherein the A and the Y moieties are separated by 4 to 15 consecutive atoms, and wherein:

when said bond represented by the dotted line is not present, X is selected from the group consisting of:

a saturated phosphonate group having the formula ($X_1$)

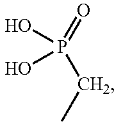

a bis-fluoro phosphonate group having the formula ($X_2$)

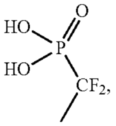

a fluoro phosphonate group having the formula ($X_3$)

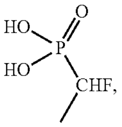

a saturated carboxylate group having the formula ($X_4$)

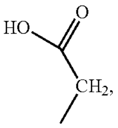

and a malonate group having the formula

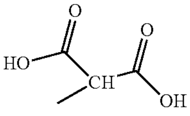

($X_5$), when said bond represented by the dotted line is present, X is selected from the group consisting of:

an unsaturated phosphonate group having the formula

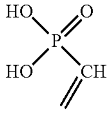

($X_6$), and an unsaturated carboxylate group having the formula

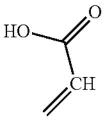

($X_7$).

All the particular embodiments disclosed previously for formula (1) apply mutatis mutandis for formula (I), and are therefore not repeated therein.

In particular, said linker L is as defined previously in formula (1), and further comprises a terminal chemical reactive group Z.

Typically, said chemical reactive group Z is selected from the group consisting of any functional group capable of binding by a covalent bond directly or after activation, to at least one of the functions naturally present or artificially introduced onto Y. By way of non-limitative examples of reactive chemical functions appropriate to the purposes of the invention, there can be mentioned in particular the functions carboxylic acid and its salts, sulphonic acid and its salts, acid anhydride, acid chloride, ester (alkyl ester, p-nitrophenyl ester, succinimidyl ester, sulphosuccinimidyl ester, etc.), azido (acyl azide, azidonitrophenyl, etc.), hydrazide, 3-acyl-1,3-thiazolidine-2-thione, amine, substituted amine, O-alkyl hydroxylamine, quaternary ammonium, isocyanate, isothiocyanate, hydrazine, phthalimido, maleimide, haloacetamide, monochlorotriazine, dichlorotriazine, mono- or dihalogenated pyridine, mono- or dihalogenated diazine, aziridine, thiol, sulphonyl chloride, vinylsulphone, disulphide, methanethiosulphonate, hydroxyl, phosphoramidite, epoxy, aldehyde, carbonate, glyoxal, imidazolyl.

In a particular embodiment, said chemical reactive group Z is a carbonyl-reactive group. More particularly, said carbonyl-reactive group is selected from the group consisting of hydrazide and O-alkyl hydroxylamine. The reaction between said hydrazide or O-alkyl hydroxylamine group with a carbonyl group of Y form respectively an acylhydrazone or an oxime linkage. This type of chemical groups is typically useful for linking glycoproteins: the carbonyl groups (either naturally present or induced by oxidation of hydroxyl functions of the glycosyl chains of the glycoprotein) available on the oligosaccharide moieties of the glycoprotein are reacted with the carbonyl-reactive groups of the compounds according to the invention.

In a particular embodiment of the invention, the compounds of formula (I) according the invention are selected from the group consisting of:

(II)

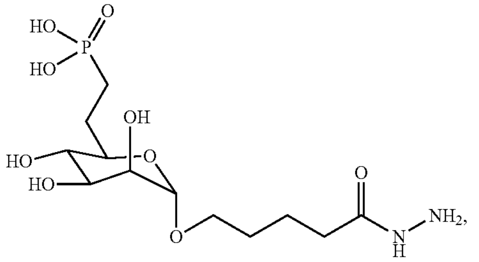

(III)

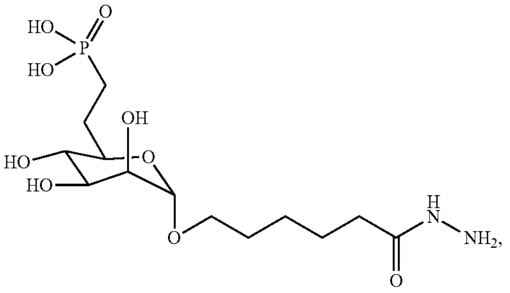

(IV)

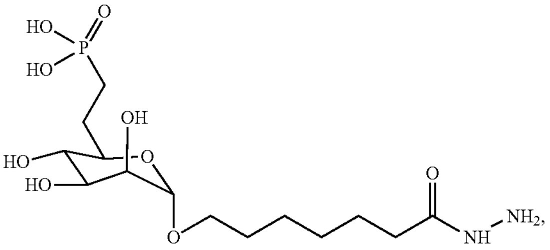

(V)

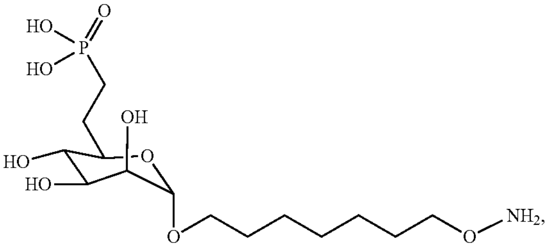

-continued (VI)

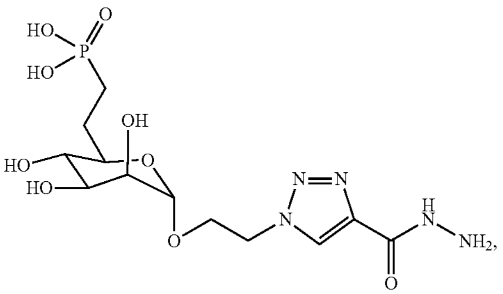

(VII)

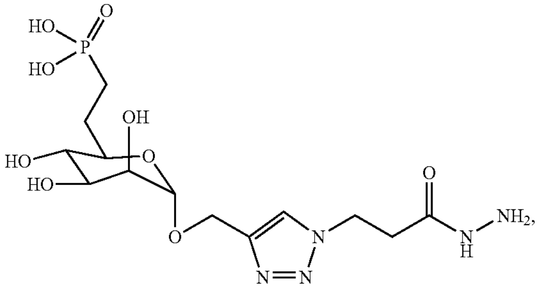

(VIII)

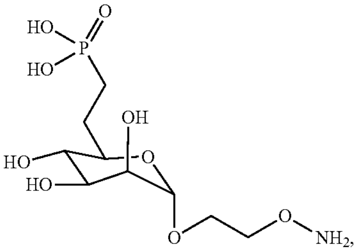

(IX)

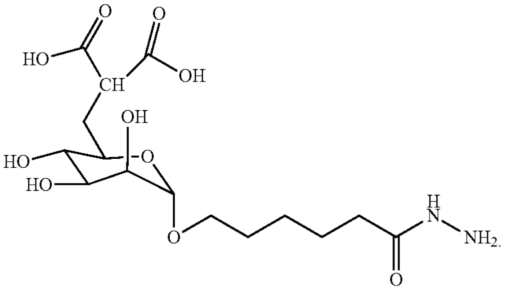

Another object of the invention relates to a method for producing a conjugate according to the invention, said method comprising the step of reacting a product of interest Y selected from the group consisting of glycoproteins, nanoparticles and labels for medical imaging, with a compound having the formula (I)

(I)

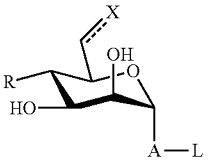

wherein said compound having formula (I) is as defined previously.

Once Y and the compound having formula (I) have reacted together, a conjugate according to the invention is formed, wherein said conjugate is a product of interest Y conjugated to said compound of formula (I) via a linker L according to the invention, said linker L comprising the remainder of the chemical reactive group which has reacted with Y. This remainder of the chemical reactive group Z is typically the T moiety according to the invention.

In a particular embodiment, said method for producing a conjugate according to the invention further comprises, before said step of reacting, a step of activating a chemical function of Y, said step of activating allowing the chemical reactive group Z of the linker L to react with the chemical function of Y. For example, activating a chemical function of a glycoprotein may consist of oxidizing hydroxyl functions of the glycosyl chains to obtain carbonyl functions (for instance by treating the glycoprotein with $NaIO_4$).

The invention further relates to conjugates obtainable by the method for producing a conjugate according to the invention and to their applications as described previously.

Throughout the description of the invention, and for simplifying the representation of the molecules, the analogues of the phosphate groups of M6P and the M6P analogues are represented in their hydrogenated form. However, the invention also pertains to the salts of these molecules.

Further aspects and advantages of this invention will be disclosed in the following figures and examples, which should be regarded as illustrative and not limiting the scope of this application.

EXAMPLES

1.1. Synthesis and Characterization of High Potent M6P Analogues

The synthesis and characterization of high potent M6P analogues (M6 Pa) were realized by replacing phosphate group by phosphonate, malonate or carboxylate group [Vidal S et al., Bioorg Med. Chem. 10, 4051, 2002; Jeanjean A et al., Bioorg Med. Chem. 14, 2575, 2006; Jeanjean A et al., Bioorg Med Chem. Lett. 18, 6240, 2008].

1.2. Binding Assay to CI-M6PR of M6P Analogues

The binding assays of the M6 Pa were performed using biotinylated CI-M6PR. Briefly, the CI-M6PR, purified on a phosphomannan-sepharose affinity column was biotinylated by N-hydroxysuccinimide biotin. The binding of the biotinylated CI-M6PR(CI-M6PRb) to pentamannose 6-phosphate (PMP) previously adsorbed on a microtitre plate was displaced by increasing concentrations of M6 Pa. The bound CI-M6PRb was then determined using the streptavidin/peroxidase couple and OPD substrate by optical density measurements. In control experiments the method was standardized by determining of the maximal concentration of the PMP adsorbed to the microtitre plate and the CI-M6PRb concentration required to saturate the adsorbed PMP [Jeanjean A et al., *Bioorg Med Chem* 14: 3575-82, 2006].

Figure 1:
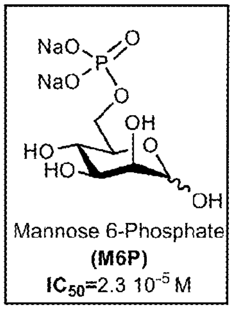
FIG. 1: Molecular structure of M6P analogues.
Figure 1:
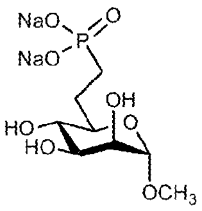
Figure 1:
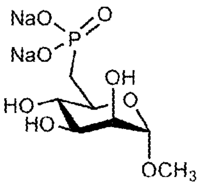
Figure 1:
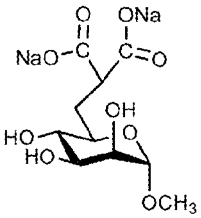
Figure 1:
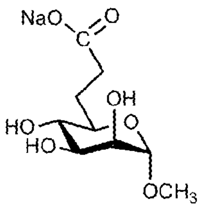

FIG. 1 shows that phosphonate 1 and malonate 3, two isosteric analogues of M6P have a higher binding affinity for CI-M6PR than that of natural M6P. In contrast, non isosteric analogues, such as phosphonate 2, are not recognized by CI-M6PR. On the other hand, carboxylate 4 shows a lower binding affinity for CI-M6PR than malonate 3. These results demonstrate that phosphonate 1 and malonate 3 present a high potential for targeting cells that express CI-M6PR.

1.3. Modelling of the M6P-Analogues Docking in the CI-M6PR Binding Pocket

The crystal structure of CI-M6PR in complex with the corresponding natural ligand was obtained from the crystallographic data files (Protein Data Bank, http://www.rcsb.org/, ID code 1SZ0). We constructed the M6P analogues based on the heavy M6P structure (heteroatom M6P500) with the ligand design module software. Ligand docking was initially carried through the superposition of the M6P analogue structure onto the M6P agonist structure. In order to equilibrate the complex, the ligand-receptor complex was then submitted to energy minimization using conjugated gradients for 2000 steps at 300° K and a harmonic potential was used for bond energies until the maximum derivative was less than 0.07 kcal/Å. Molecular dynamic simulation using the Discover module was then performed. We applied the constant force field and the conjugate gradient algorithm together with a cut-off distance of 25 Å. Tether constraint was applied to the backbone of the receptor [Jeanjean A. et al. *Curr Med. Chem.* 14: 2945-53, 2007].

Figure 2:
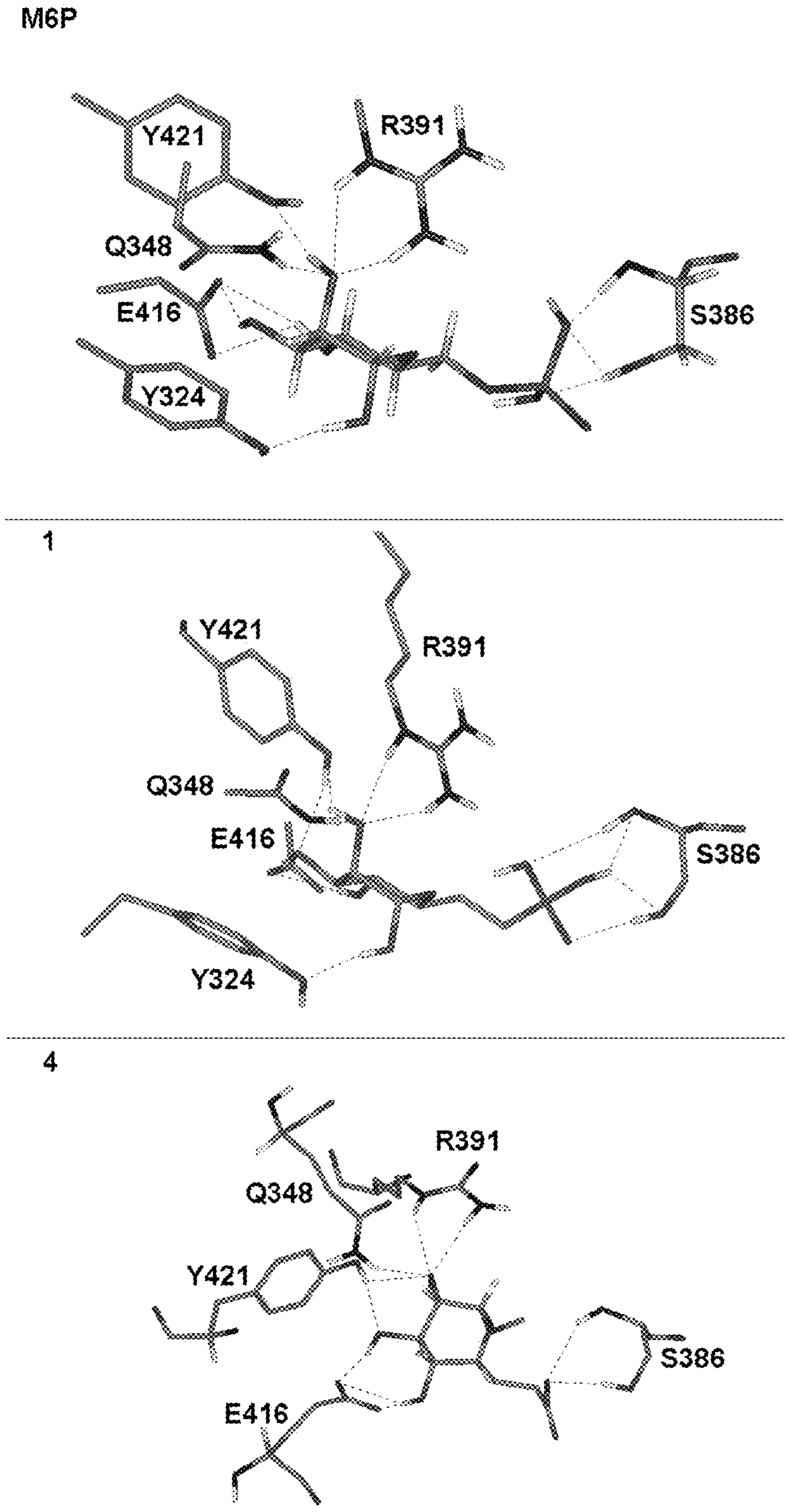
FIG. 2: Potential hydrogen bonds of M6P docked in CI-M6PR ligand binding pocket.

FIG. 2 shows that natural M6P displays 11 potential hydrogen bonds and only 6 different anchorage points whereas the phosphonate 1 analogue exhibits 12 potential hydrogen bonds with the essential residues in the ligand binding domain, and is anchored by 8 different positions to the CI-M6PR. In addition, malonate 3 which is characterised by two carboxylate moieties instead of a phosphate moiety forms 13 potential hydrogen bonds and has 8 anchorage points (data not shown).

By contrast, for the carboxylate 4 which displays a lower binding affinity than the M6P reference, the direct interaction of residue Y324 and the mannose was missing. Previous studies [Hancock, M. K. et al, *J Biol Chem*, 277, 11255-64, 2002] have also shown that single amino acid substitutions are involved in the ligand stability.

1.4. Biological Characterization of High Potent M6P Analogues

Pharmacological properties of a high potent analogue, phosphonate 1, were compared to M6P.

Figure 3:
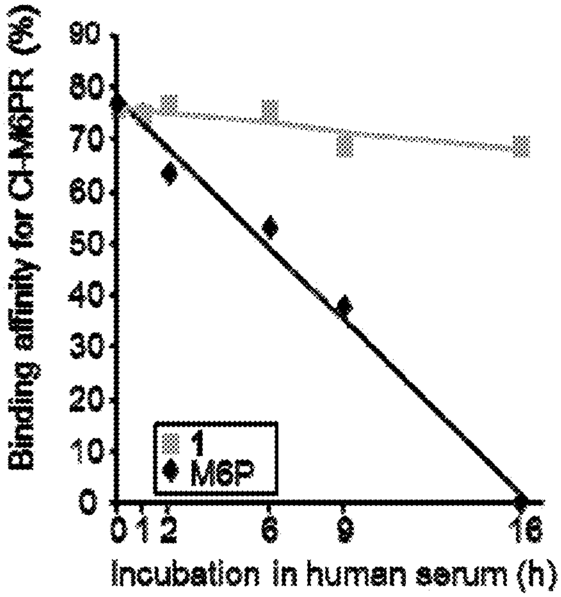
FIG. 3: Kinetic of M6P and phosphonate 1 degradation in human serum.

First, we analyzed the phosphonate 1 stability in 75% (v/v) human serum. Results show that phosphonate 1 is 10-fold more stable in serum than natural M6P (FIG. 3).

Second, phosphonate 1 effect on endocytosis via CI-M6PR was compared to that of natural M6P. Previous results have shown that a complex cathepsin D/anti-cathepsin D antibody was specifically internalised by CI-M6PR in normal human fibroblasts [Laurent-Matha V et al., *J Cell Sci.* 111: 2539-49, 1998]. The complex was here detected by immunofluorescence staining.

Figure 4:
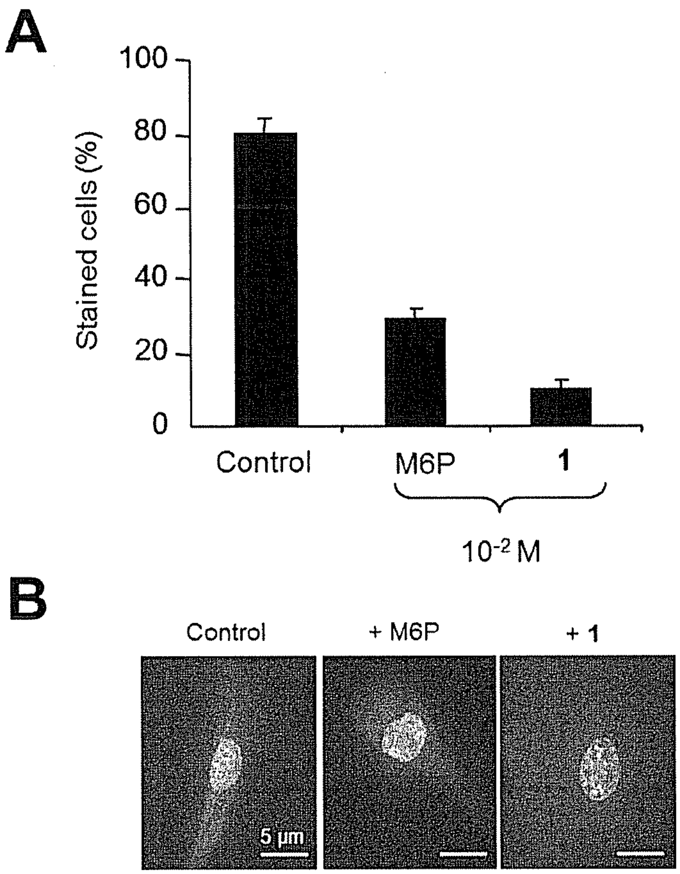
FIG. 4: Specific binding of M6P and phosphonate 1 in a human normal cell line.

FIG. 4A shows that 80% of control cells have internalized the cathepsin D/anti-cathepsin D antibody complex, whereas cells pre-incubated with 10 mM M6P or phosphonate 1 internalized only 30% and 10% respectively. This result demonstrates that phosphonate 1 has a higher binding affinity than that of M6P. FIG. 4B shows that the staining intensity of cells is lower in presence of phosphonate 1 than in presence of M6P. All these results demonstrate the high potential of phosphonate 1 in targeting CI-M6PR.

Figure 5:
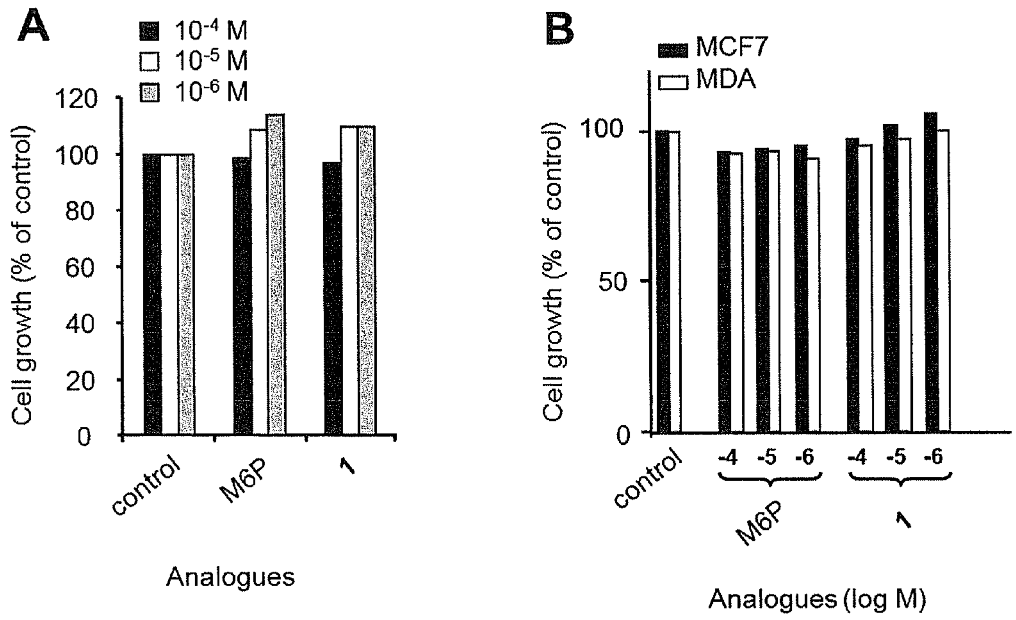
FIG. 5: No cytotoxic effect of M6P and phosphonate 1 on human normal fibroblast IMR-90 cell line (A) and on two breast cancer cell lines (B).

Third, we studied the cytotoxicity of phosphonate 1 in vitro. Normal or cancer cell lines were treated for 4 days with increasing doses of phosphonate 1. Bar graphs indicate that this compound did not induce any cytotoxicity, even at elevated concentration (0.1 mM) neither on human normal fibroblast cell line (FIG. 5A) nor on breast cancer cell lines, such as MCF7 or MDA-MB-231 (FIG. 5B).

1.5. Molecular Modelling of a Malonate 3 Analogue of M6P in the Binding Pocket of CI-M6PR, Before (FIG. 6*a*) and after (FIG. 6*b*) Coupling with a Linker (Hexane Hydrazide)

Figure 6:
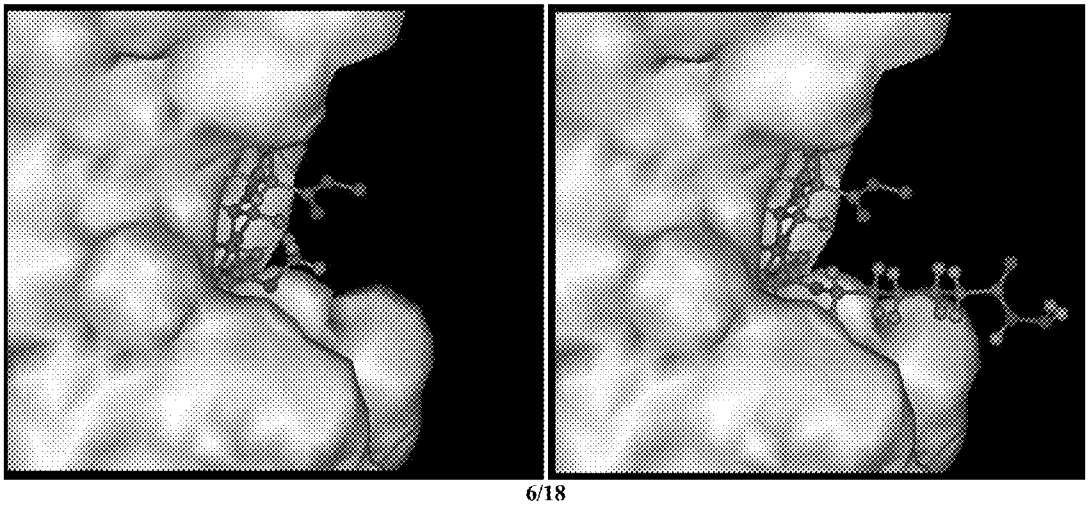
FIG. 6: Molecular modelling of malonate 3 with or without linker, docked in CI-M6PR binding pocket.

In order to eliminate or reduce the steric hindrance nearby the binding pocket of the CI-M6PR due to the grafting on a macromolecule to M6P analogues, the addition of a separating linker was proposed. FIG. 6 shows that a hexanoyl hydrazide linker allows sufficient spacing between the binding sites for M6P of the CI-M6PR and the product which has to be bound to hydrazide group. Molecular modelling studies show that a spacer of 6 to 7 Å is required in the binding pocket of CI-M6PR between M6P analogues and the macromolecule to be grafted. Spacer arm could be substituted at different positions by nitrogen or oxygen atom which could make hydrogen bonds with some residues of the ligand binding pocket such as Y324, E323, K350, Q356. This linker could be either an aliphatic chain or cycles like substituted phenyl or triazole. Thus, by this way, the binding affinity of the M6P analogues for CI-M6PR will not be altered by the grafting of a macromolecule such as a lysosomal enzyme.

1.6. Linker Syntheses and Characterizations

Figure 7:
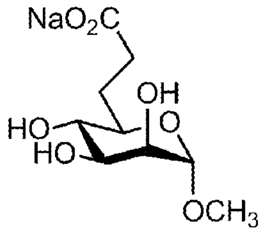
FIG. 7: Improvement of carboxylate 4 binding affinity after grafting of spacer arms.
Figure 7:
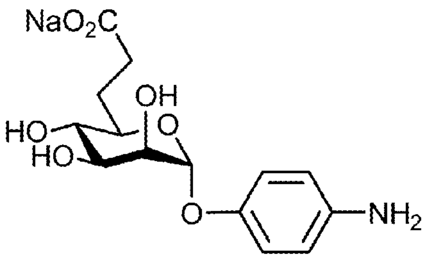
Figure 7:
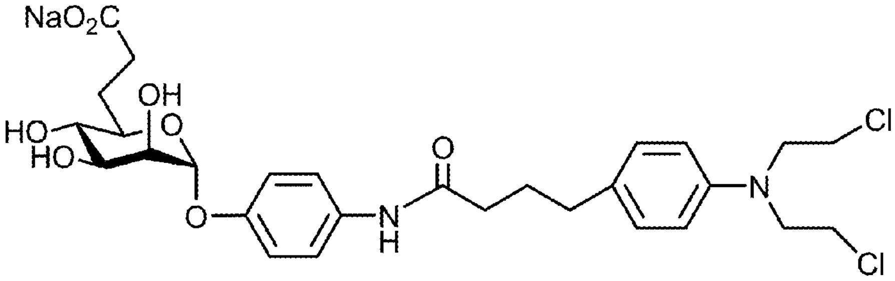

FIG. 7 shows the improvement in the binding affinity of carboxylate 4 (A) for CI-M6PR by a factor of 1.7 after grafting at aglycone position of $OPhNH_2$ (B) and by a factor of 2 after an additional grafting of a chlorambucil (C).

Figure 8:
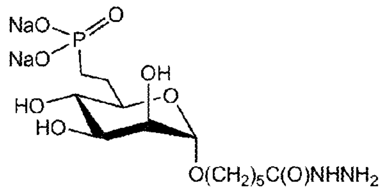
FIG. 8: Examples of spacer arms grafted on phosphonate 1 (AMFA-1, AMFA-2)
Figure 8:
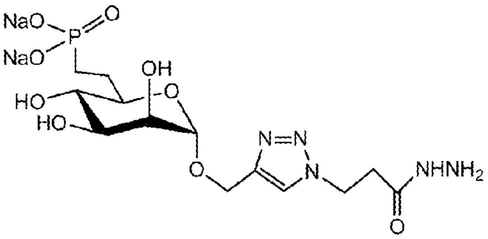
Figure 8:
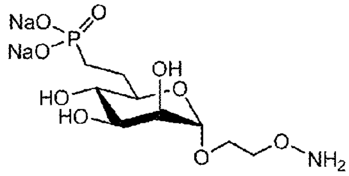
Figure 8:
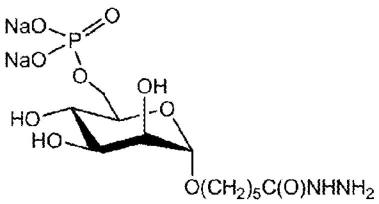
Figure 8:
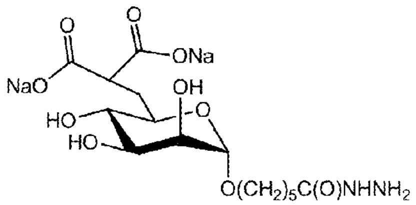

FIG. 8 describes the structure of phosphonate 1 bound to the different linkers, hexanehydrazide (AMFA-1), triazole (AMFA-2) and aminoxy (AMFA-3). These compounds (AMFA, Analogue of M6P Functionalized on Aglycone) are examples of compounds having formula (I) according to the invention. The structure of malonate 3 (AMFA-5) and M6P bound to hexanehydrazide arm is also given in FIG. 8.

1.7 Synthesis of AMFA-1, AMFA-2, AMFA-3, AMFA-5 and M6P-hexanehydrazide—FIGS. 9-13

Figure 9:
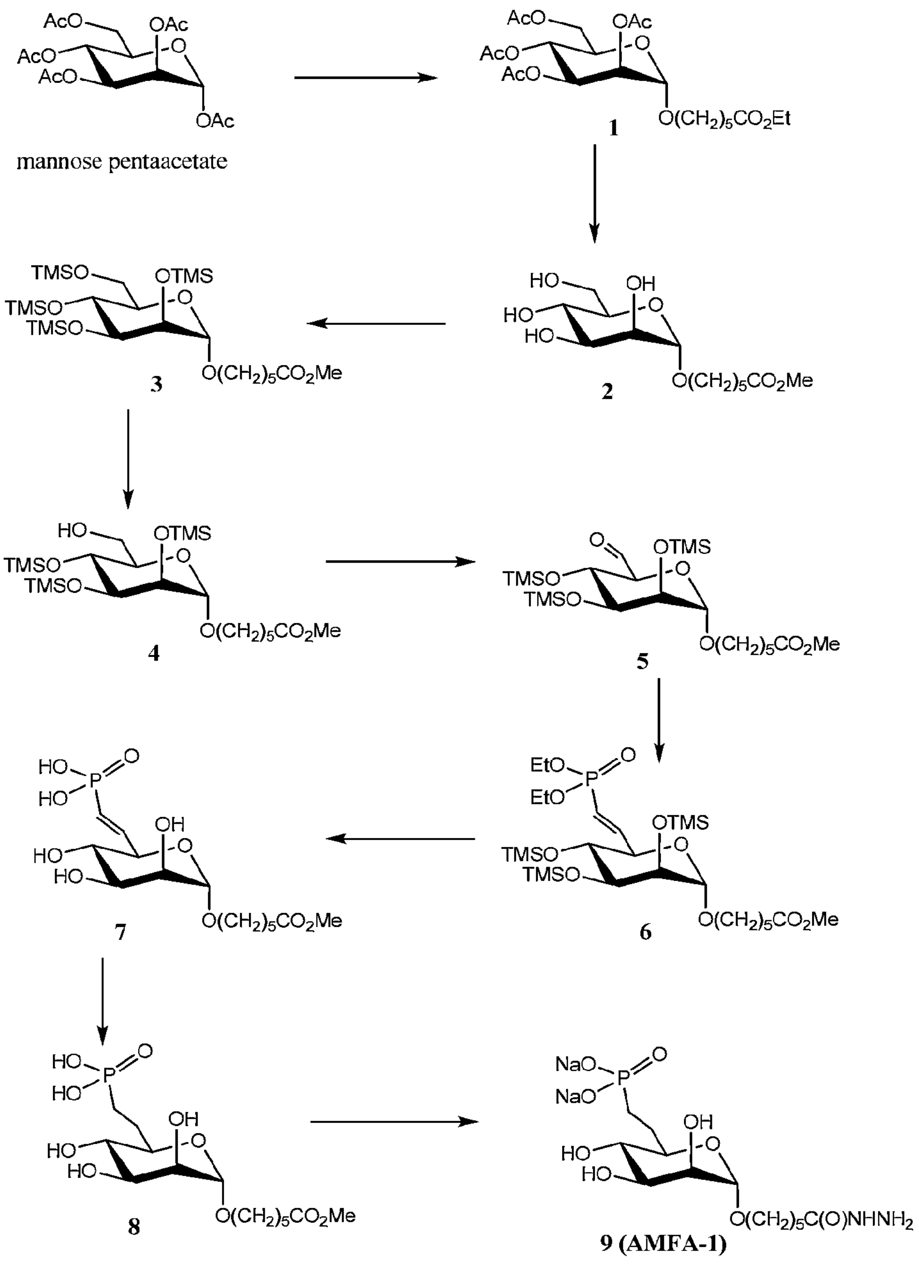
FIG. 9: Synthesis of AMFA-1.

1.7.1. Synthesis of AMFA-1 (FIG. 9)

5-ethoxycarbonylpentyl 2,3,4,6-tetra-O-acetyl-α-D-mannopyranoside 1

To mannose pentaacetate (10.00 g, 25.64 mmol) dissolved in 60 mL of $CH_2Cl_2$, ethyl 6-hydroxyhexanoate (8.3 mL, 51.28 mmol) was added at room temperature and then $BF_3.Et_2O$ at 0° C. After 4 days under stirring at room temperature, the reaction mixture was washed twice with $NaHCO_3$ (2×20 mL) and then with brine (20 mL). The organic layer was dried ($MgSO_4$) and concentrated under vacuum. Compound 1 (7.14 g, 57%) was obtained after column chromatography on silica gel (hexane/AcOEt; 6:4).

Rf=0.58 [Hexane/AcOEt (6:4)]

SM, $ESI^+$ m/z: 513 $[M+Na]^+$, 529 $[M+K]^+$

5-methoxycarbonylpentyl α-D-mannopyranoside 2

To compound 1 (3.7 g, 7.55 mmol) dissolved in 35 mL of anhydrous methanol, sodium methylate (1.6 g, 30.20 mmol) was added. After 30 min under stirring, cation exchange resin (Dowex® 50WX2, $H^+$ form, 13 g) was added. After 1 h the resin was filtered and washed with methanol. The filtrate was concentrated under reduced pressure yielding 2 (2.1 g, 100%).

Rf=0.35 [AcOEt/MeOH (9:1)]

MS, $ESI^+$ m/z: 331 $[M+Na]^+$, 347 $[M+K]^+$

5-methoxycarbonylpentyl 2,3,4,6-tetra-O-trimethylsilyl-α-D-mannopyranoside 3

$Et_3N$ (8.85 mL, 63.40 mmol), then trimethylsilyl chloride (7.1 mL, 54.48 mmol) and a catalytic amount of DMAP were added successively at 0° C. to compound 2 (2.10 g, 6.81 mmol) dissolved in 30 mL of THF. The reaction mixture was stirred for 30 h, then the solvents were evaporated and the crude dissolved in 150 mL of $CH_2Cl_2$. The organic layer was washed with brine (100 mL), dried over $MgSO_4$, filtered and evaporated under reduced pressure to lead to 3 (1.62 g, 40%).

Rf=0.7 [EP/$Et_2O$ (9:1)]

MS, $ESI^+$ m/z: 619 $[M+Na]^+$, 635 $[M+K]^+$

5-methoxycarbonylpentyl 2,3,4-tri-O-trimethylsilyl-α-D-mannopyranoside 4

To 3 (2.45 g, 4.11 mmol) in 2 mL of methanol, a methanolic solution of $K_2CO_3$ (36 mL, 0.11 mM) was added at 0° C. After stirring at 0° C. for 30 min, the reaction mixture was diluted with 170 mL of $CH_2Cl_2$. The organic layer was washed with 170 mL of brine. The aqueous layer was extracted with 150 mL of $CH_2Cl_2$. The organic layers were combined then dried over $MgSO_4$, filtered, concentrated under vacuum and purified by column chromatography on silica gel (Hexane/$Et_2O$, 8:2+$Et_3N$ (1%)) affording 4 (1.29 g, 60%).

Rf=0.37 [EP/$Et_2O$ (7:3)]

MS, $ESI^+$ m/z: 547 $[M+Na]^+$, 563 $[M+K]^+$ 5-methoxycarbonylpentyl(E)-2,3,4-tri-O-trimethylsilyl-6-deoxy-6-diethoxyphosphinylmethylene-α-D-mannopyranoside 6

To oxalyl chloride (73 $10^{-3}$ mL, 0.84 mmol) dilute in 1 mL of THF, DMSO (135 $10^{-3}$ mL, 1.9 mmol) was added at −78° C. After 10 min, 4 (0.400 g, 0.76 mmol) in 2 mL of THF was added dropwise at −78° C. After 20 min, $Et_3N$ (533 $10^{-3}$ mL, 3.8 mmol) was added. The reaction mixture was stirred at −78° C. for 10 min then left at RT for 30 min. Solvents were removed by evaporation and the residue dissolved in $CH_2Cl_2$ (20 mL). The organic layer was washed with brine (20 mL), dried ($MgSO_4$), filtrated and concentrated under vacuum. The crude aldehyde 5 was used for the next step without further purification.

To NaH (80%, 0.045 g, 1.55 mmol) suspended in 10 mL of THF, tetraethyl methylenediphosphonate (385 $10^{-3}$ mL, 1.55 mmol) was added dropwise at RT. After 1 h under stirring, a THF (5 mL) solution of crude aldehyde 5 was added at RT. After 1 h 15 the THF was evaporated and the residue dissolved in $CH_2Cl_2$ (40 mL). The organic layer was washed with brine (2×10 mL), dried over $MgSO_4$, evaporated under reduced pressure and purified by column chromatography on silica gel (AcOEt/PE, 8:2) leading to 6 (0.130 g, 30%).

Rf=0.72 [AcOEt/EP, (8:2)]

MS, $ESI^+$ m/z: 657 $[M+H]^+$, 679 $[M+Na]^+$, 695 $[M+K]^+$ 5-methoxycarbonylpentyl(E)-6-deoxy-6-dihydroxyphosphinylmethylene-α-D-mannopyranoside 7

To compound 6 (0.29 g, 0.44 mmol) dissolved in $CH_3CN$ (3 mL), pyridine (89 $10^{-3}$ mL, 1.1 mmol) and then trimethylsilyl bromide (700 $10^{-3}$ mL, 4.4 mmol) were added. The reaction mixture was stirred for 6 h at RT and solvents were evaporated. The residue was dissolved in MeOH and excess of pyridinium salts were removed by filtration. The filtrate was treated with cation exchange resin (Dowex® 50WX2, $H^+$ form, 0.5 g) and then purified by column chromatography on silica gel 100 $C_{18}$-reversed phase (Fluka) (eluent: water then methanol) leading to compound 7 (0.10 g, 59%).

Rf=0.33 [AcOEt/MeOH, (6:4)]

SM, $ESI^+$ m/z: 385 $[M+H]^+$, 407 $[M+Na]^+$ 5-methoxycarbonylpentyl 6-deoxy-6-dihydroxyphosphinylmethyl-α-D-mannopyranoside 8

7 (0.048 g, 0.124 mmol) in 3 mL of methanol/$H_2O$ (2:1) was stirred for 18 h under an atmosphere of hydrogen in the presence of Pd/C (10%, 8 mg). The reaction mixture was filtered through a Celite pad and evaporated under vacuum to lead to 8 (0.046 g, 100%).

Rf=0.51 [AcOEt/MeOH, (9:1)]

MS, $ESI^+$ m/z: 387 $[M+H]^+$, 409 $[M+Na]^+$, 425 $[M+K]^+$ 5-hydrazinocarbonylpentyl 6-deoxy-6-dihydroxyphosphinylmethyl-α-D-mannopyranoside disodium salt 9 or AMFA-1

To 8 (0.045 g, 0.12 mmol) in 2 mL of MeOH, monohydrate hydrazine (28 $10^{-3}$ mL, 0.58 mmol) was added. After 18 h the solvents were evaporated and the residual hydrazine was co-evaporated 4 times with ethanol. The crude was purified by a chromatography on silica gel 100 $C_{18}$-reversed phase (Fluka) (eluent: $H_2O$) and then treated by cation exchange resin (Dowex® 50WX2, $Na^+$ form, 0.200 g). The resin was filtered and 9 was obtained after lyophilisation (0.035 g, 68%).

Rf=0.44 [MeOH]

$[\alpha]_D^{20}$=+69.12° (c 1/$D_2O$)

Figure 10:
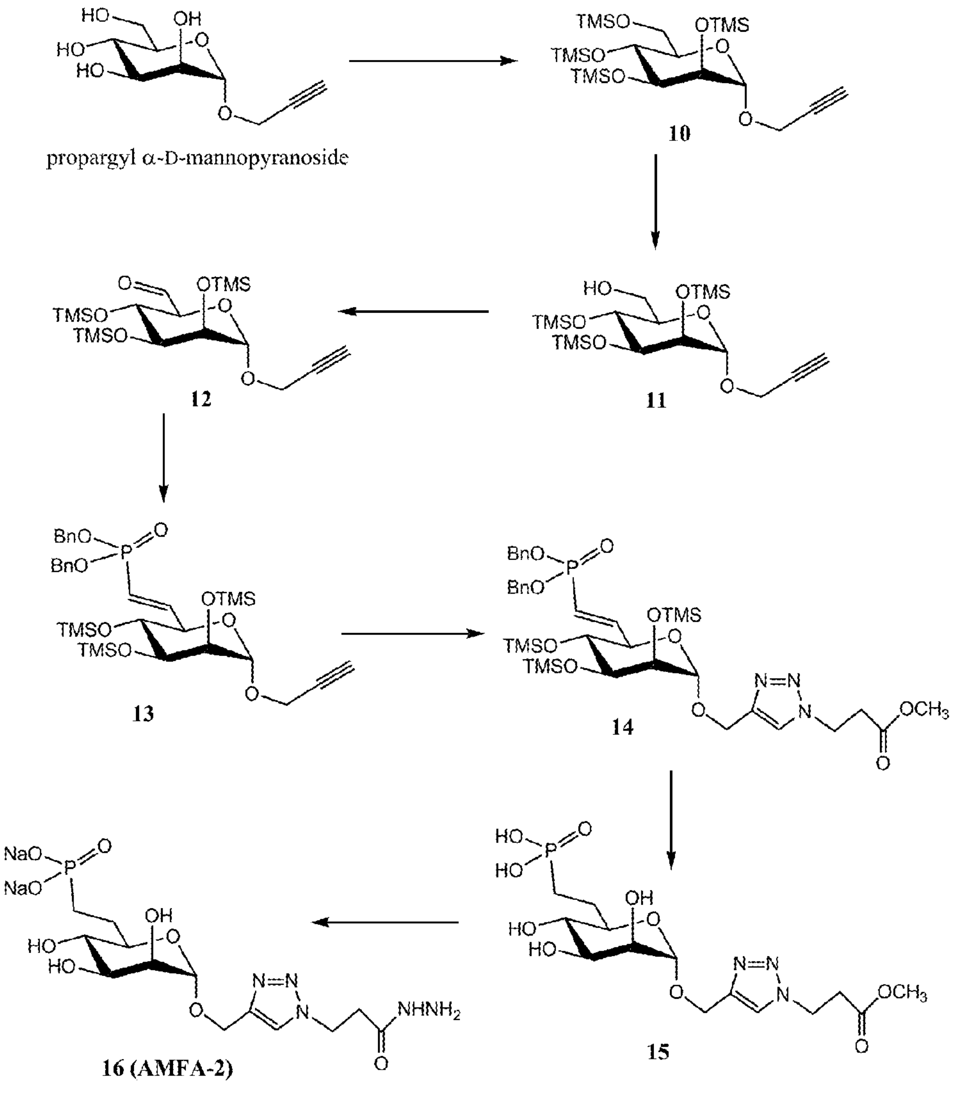
FIG. 10: Synthesis of AMFA-2.

MS, $ESI^-$ m/z: 385 $[M-2Na^++H]^+$ 1.7.2. Synthesis of AMFA-2 (FIG. 10)

Propargyl 2,3,4,6-tetra-O-trimethylsilyl-α-D-mannopyranoside 10

10 was prepared according to the same procedure as for 3.

Rf=0.95 [EP/$Et_2O$ (7:3)]

Yield=95%

MS, $ESI^+$ m/z: 529 $[M+Na]^+$

Propargyl 2,3,4-tri-O-trimethylsilyl-α-D-mannopyranoside 11

The compound 11 was prepared according to the same procedure as for 4.

Rf=0.37 [EP/$Et_2O$ (9:1)]

Yield=57%

MS, $ESI^+$ m/z: 457 $[M+Na]^+$

Propargyl(E)-2,3,4-Tri-O-trimethylsilyl-6,7-dideoxy-7-dibenzyloxyphosphinyl-α-D-manno-hept-6-enopyranoside 13

The phosphonate 13 was prepared according to the same procedure as for 7 via the preparation of the aldehyde 12 prepared following the same procedure as for 6. In order to obtain the dibenzyl phosphonate 13 the tetrabenzylmethylenediphosphonate was used instead of the tetraethylmethylenediphosphonate.

Rf=0.83 [$Et_2O$/EP (8:2)]

Yield=63%

MS, $ESI^+$ m/z: 691 $[M+H]^+$, 713 $[M+Na]^+$ (Methoxycarbonylethyl)-1H-1,2,3-triazol-4-yl-methyl (E)-2,3,4-Tri-O-trimethylsilyl-6,7-dideoxy-7-dibenzyloxyphosphinyl-α-D-manno-hept-6-enopyranoside 14

To phosphonate 13 (250 mg, 0.362 mmol) and methyl 3-azidopropionate (37 μL, 0.435 mmol) in $CH_2Cl_2$ (2 mL), $Cu(CH_3CN)_4PF_6$ (135 mg, 0.362 mmol) and 2,6-lutidine (5 μL, 0.0362 mmol) were successively added. The mixture was stirred for 20 h at room temperature. After evaporation of the solvent, the crude was directly purified by column chromatography on silica gel (eluent: $CH_2Cl_2$ then $CH_2Cl_2$/MeOH, 99:1 and 98:2) to afford 14 (236 mg, 80%).

Rf=0.65 [$CH_2Cl_2$/MeOH, (98:2)]

MS, $ESI^+$ m/z: 820 $[M+H]^+$ (Methoxycarbonylethyl)-1H-1,2,3-triazol-4-yl-methyl 6-Deoxy-6-dihydroxyphosphinylmethylene-α-D-mannopyranoside 15

A mixture of phosphonate 14 (130 mg, 0.159 mmol) and 20 mg of Pd/C (10%) in 6 mL of EtOH/$H_2O$ (5:1) was stirred under a hydrogen atmosphere (20 bars). After 16 h, the catalyst was removed by filtration on Celite pad and the filtrate was concentrated under reduced pressure to afford 15 (65 mg, 96%).

Rf=0.17 [AcOEt/MeOH, (7:3)]

MS, $ESI^-$ m/z: 424 $[M-H]^-$

Disodium salt of (Hydrazinocarbonylethyl)-1H-1,2,3-triazol-4-yl-methyl 6-Deoxy-6-dihydroxyphosphinylmethylene-α-D-mannopyranoside 16 or AMFA-2

AMFA-2 was prepared following the procedure applied to AMFA-1

Rf=0.23 [MeOH/AcOEt, (7:3)]

Yield=30%

Figure 11:
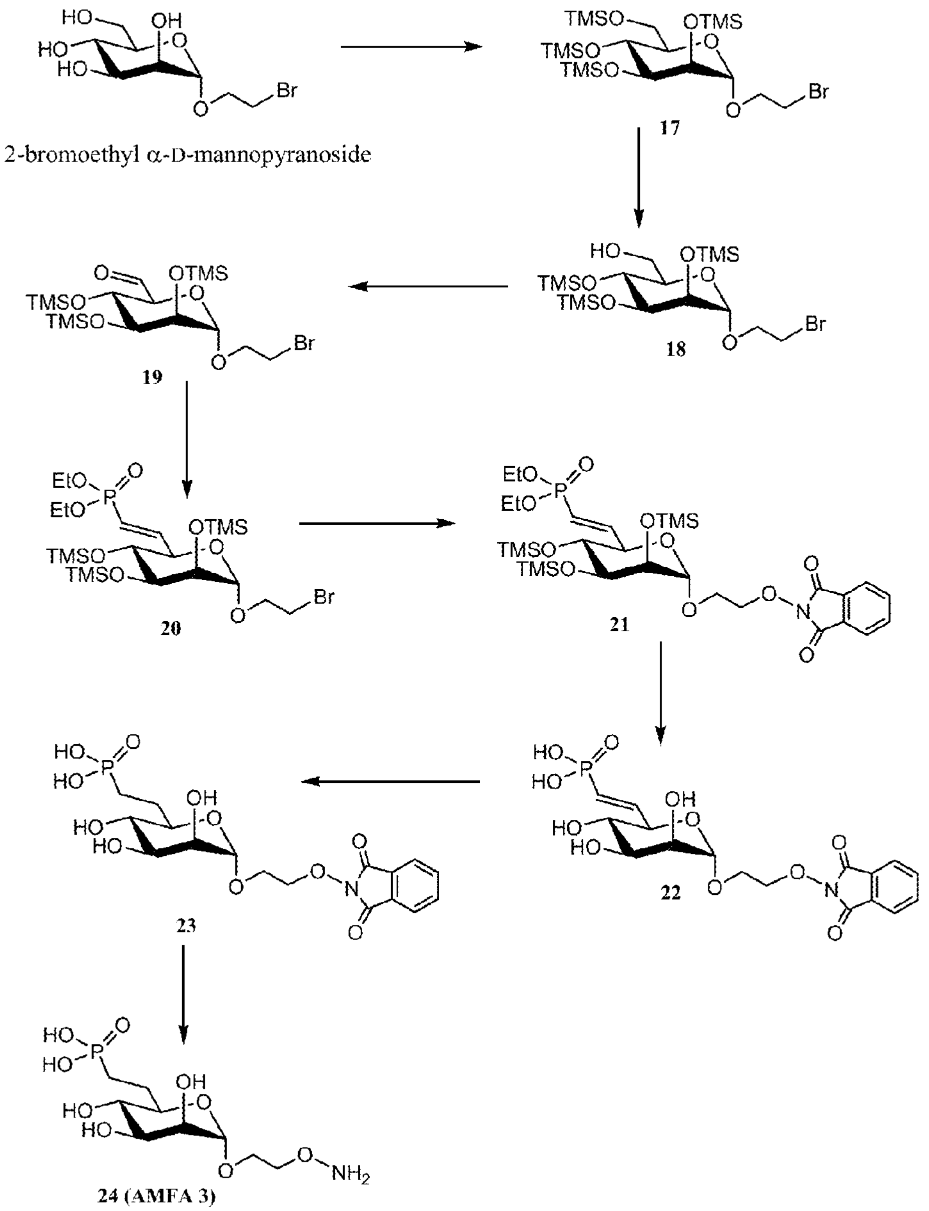
FIG. 11: Synthesis of AMFA-3.

MS, $ESI^-$ m/z: 424 $[M-2Na+H]^-$ 1.7.3. Synthesis of AMFA-3 (FIG. 11)

2-bromoethyl 2,3,4,6-tetra-O-trimethylsilyl-α-D-mannopyranoside 17

17 was prepared according to the same procedure as for 3.

Rf=0.88 [EP/$Et_2O$ (9:1)]

Yield=87%

MS, $ESI^+$ m/z: 597 $[M+Na]^+$ 2-bromoethyl 2,3,4-tri-O-trimethylsilyl-α-D-mannopyranoside 18

The compound 18 was prepared according to the same procedure as for 4.

Rf=0.46 [EP/$Et_2O$ (6:4)]

Yield=48%

MS, $ESI^+$ m/z: 525 $[M+Na]^+$ 2-bromoethyl(E)-2,3,4-tri-O-trimethylsilyl-6,7-dideoxy-7-diethyloxyphosphinyl-α-D-manno-hept-6-enopyranoside 20

The phosphonate 20 was prepared according to the same procedure as for 7 via the preparation of the aldehyde 19 prepared following the same procedure as for 6.

Rf=0.53 [$Et_2O$]

Yield=60%

MS, $ESI^+$ m/z: 635 $[M+H]^+$ 2-(phthalimidoxy)ethyl (E)-2,3,4-tri-O-trimethylsilyl-6,7-dideoxy-7-diethyloxyphosphinyl-α-D-manno-hept-6-enopyranoside 21

N-hydroxyphthalimide (468 mg, 2.9 mmol) was added to NaH (109 mg, 3.3 mmol) in 50 mL of anhydrous DMF. After 1 h under stirring, the phosphonate 20 (1.21 g, 1.9 mmol) dissolved in 10 mL of DMF was added dropwise to the solution. The red solution was stirred 26 h at 40° C. then quenched with $Et_2O$ (300 mL). The organic layer was washed with brine (150 mL), then dried ($MgSO_4$), concentrated under reduced pressure and purified by column chromatography on silica gel ($Et_2O$/EP 8/2, 9/1 then $Et_2O$) affording 21 (835 mg, 61%).

Rf=0.55 [AcOEt/MeOH, (8:2)]

Yield=61%

MS, $ESI^+$ m/z: 718 $[M+H]^+$, 740 $[M+Na]^+$ 2-(phthalimidoxy)ethyl (E)-6,7-dideoxy-7-diethyloxyphosphinyl-α-D-manno-hept-6-enopyranoside 22

22 was prepared according to the same procedure as for 7

Rf=0.63 [AcOEt/MeOH, (5:5)]

Yield=45%

MS, $ESI^-$ m/z: 444 $[M-H]^-$ 2-(phthalimidoxy)ethyl 6-deoxy-6-dihydroxyphosphinylmethylene-α-D-mannopyranoside 23

Reduction of the double bond of 22 was made under the same conditions as for 8

Rf=0.61 [AcOEt/MeOH, (5:5)]

Yield=98%

MS, $ESI^-$ m/z: 446 $[M-H]^-$

Disodium salt of 2-(aminoxy)ethyl 6-deoxy-6-dihydroxyphosphinylmethylene-α-D-mannopyranoside 24 or AMFA-3

To 23 (0.065 g, 0.145 mmol) in 5 mL of MeOH/$H_2O$ (1:1) was added monohydrate hydrazine (21.2 $10^{-3}$ mL, 0.436 mmol). After 3 h the solvents were evaporated. The crude was purified by a chromatography on silica gel 100 $C_{18}$-reversed phase (Fluka) (eluent: $H_2O$) and then treated by cation exchange resin (Dowex® 50WX2, $Na^+$ form, 0.200 g). The resin was filtered and 24 was obtained after lyophilisation (0.035 g, 40%).

Rf=0.42 [MeOH]

Yield=40%

Figure 12:
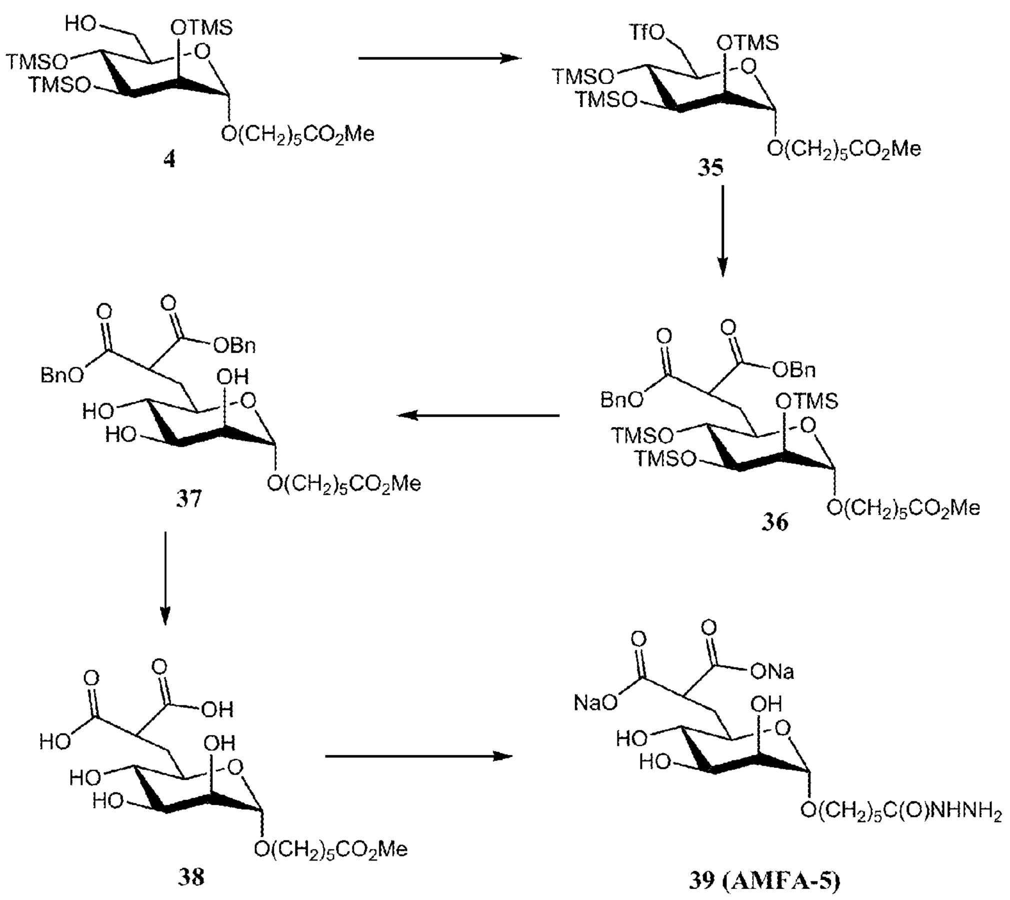
FIG. 12: Synthesis of AMFA-5.

MS, $ESI^-$ m/z: 316 $[M-2Na+H]^-$ 1.7.4. Synthesis of AMFA-5 (FIG. 12)

[5-methoxycarbonylpentyl 6,7-dideoxy-7-(benzyloxycarbonyl)-α-D-manno-octopyranoside]benzyl uronate 37

Trifluoromethansulfonic anhydride (106 $10^{-3}$ mL, 0.697 mmol) was added drop by drop at −40° C. to 4 (300 mg, 0.57 mmol) and 2,6-di-tert-butyl-4-methylpyridine (153 mg, 0.744 mmol) dissolved in $CH_2Cl_2$ (3 mL). The mixture was stirred for 30 min then dilute with $CH_2Cl_2$ and organic layer was washed with water dried over $MgSO_4$ and concentrated under vacuum. Excess of 2,6-di-tert-butyl-4-methylpyridine was removed by precipitation in hexane. The crude triflate 35 was used during next step without further purification.

To a solution of triflate 35 (328 mg, 0.50 mmol) in THF (3 mL) was added at RT the sodium salt of the dibenzyl malonate (0.720 mmol) dilute in THF (15 mL). After completion of reaction, the mixture containing 36 was treated by HCl 1N in order to desilylate the malonate 36. After 10 min, the mixture was neutralized by $NaHCO_3$ aq. The aqueous layer was extracted twice with $CH_2Cl_2$. The organic layer was dried over $MgSO_4$, filtered and concentrated under vacuum. The crude was purified by column chromatography on silica gel ($CH_2Cl_2$, then $CH_2Cl_2$/MeOH, 9:1) leading to 37 (0.075 g, 23%).

Rf=0.52 [$CH_2Cl_2$/MeOH, (9:1)]

SM, $ESI^+$ m/z: 597 $[M+Na]^+$

[5-methoxycarbonylpentyl 6,7-dideoxy-7-(carboxy)-α-D-manno-octopyranoside]uronic acid 38

The debenzylation of 37 was realized according to the same procedure as for the preparation of the phosphonate 15.

Rf=0.34 [AcOEt/MeOH, (8:2)]
Yield=93%
SM, $ESI^+$ m/z: 395 $[M+H]^+$
SM, $ESI^+$ m/z: 393 $[M-H]^-$

[5-methoxycarbonylpentyl 6,7-dideoxy-7-(carboxy)-α-D-manno-octopyranoside]uronate disodium salt 39 or AMFA-5

Figure 13:
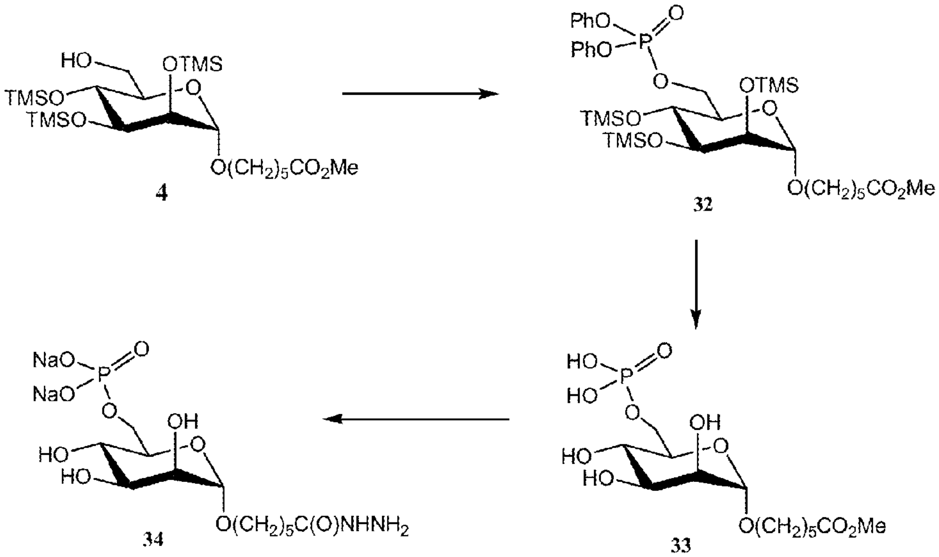
FIG. 13: Synthesis of M6P-hexanehydrazide.

Starting from 38, the malonate 39 was prepared following the procedure applied to AMFA-1.
Rf=0.55 [MeOH]
Yield=56%
MS, $ESI^-$ m/z: 393 $[M-2Na+H]^-$ 1.7.5. Synthesis of M6P-Hexanehydrazide (i.e. Compound 34) (FIG. 13)

5-methoxycarbonylpentyl 2,3,4-tri-O-trimethylsilyl-6-diphenoxyphosphinyl-α-D-mannopyranoside 32

Diphenylchlorophosphate (143 $10^{-3}$ mL, 0.69 mmol), $Et_3N$ (112 $10^{-3}$ mL, 0.8 mmol) and a catalytic quantity of DMAP were added to 4 (300 mg, 0.57 mmol) dissolved in $CH_2Cl_2$ (5 mL). The mixture was stirred for 5 h then solvents were evaporated the crude was purified by column chromatography on silica gel (PE/$Et_2O$, 6:4 then 5:5) leading to 6 (0.42 g, 95%).
Rf=0.63 [Hexane/AcOEt, (5:5)]
SM, $ESI^+$ m/z: 779 $[M+Na]^+$ 5-methoxycarbonylpentyl 6-phosphate-α-D-mannopyranoside 33

$PtO_2$ (70 mg) was added to 32 (0.410 g, 0.54 mmol) dissolved in ethanol (15 mL) and the reaction mixture was stirred for 6 h at RT under an atmosphere of $H_2$. The reaction mixture was filtered through a Celite pad and evaporated under vacuum to lead to 33 (0.207 g, 97%).
Rf=0.12 [AcOEt/MeOH (8:2)]
SM, $ESI^-$ m/z: 387 $[M-H]^-$, 775 $[2M-H]^-$ 5-hydrazinocarbonylpentyl 6-phosphate-α-D-mannopyranoside disodium salt 34

Starting from 33, the phosphate 34 was prepared following the procedure applied to AMFA-1.
Rf=0.28 [Isopropanol/$NH_4OH$, (5:5)]
Yield=25%
MS, $ESI^-$ m/z: 387 $[M-2Na+H]^-$ 1.8. Pharmacological Properties Analysis of AMFA-1

Figure 14:
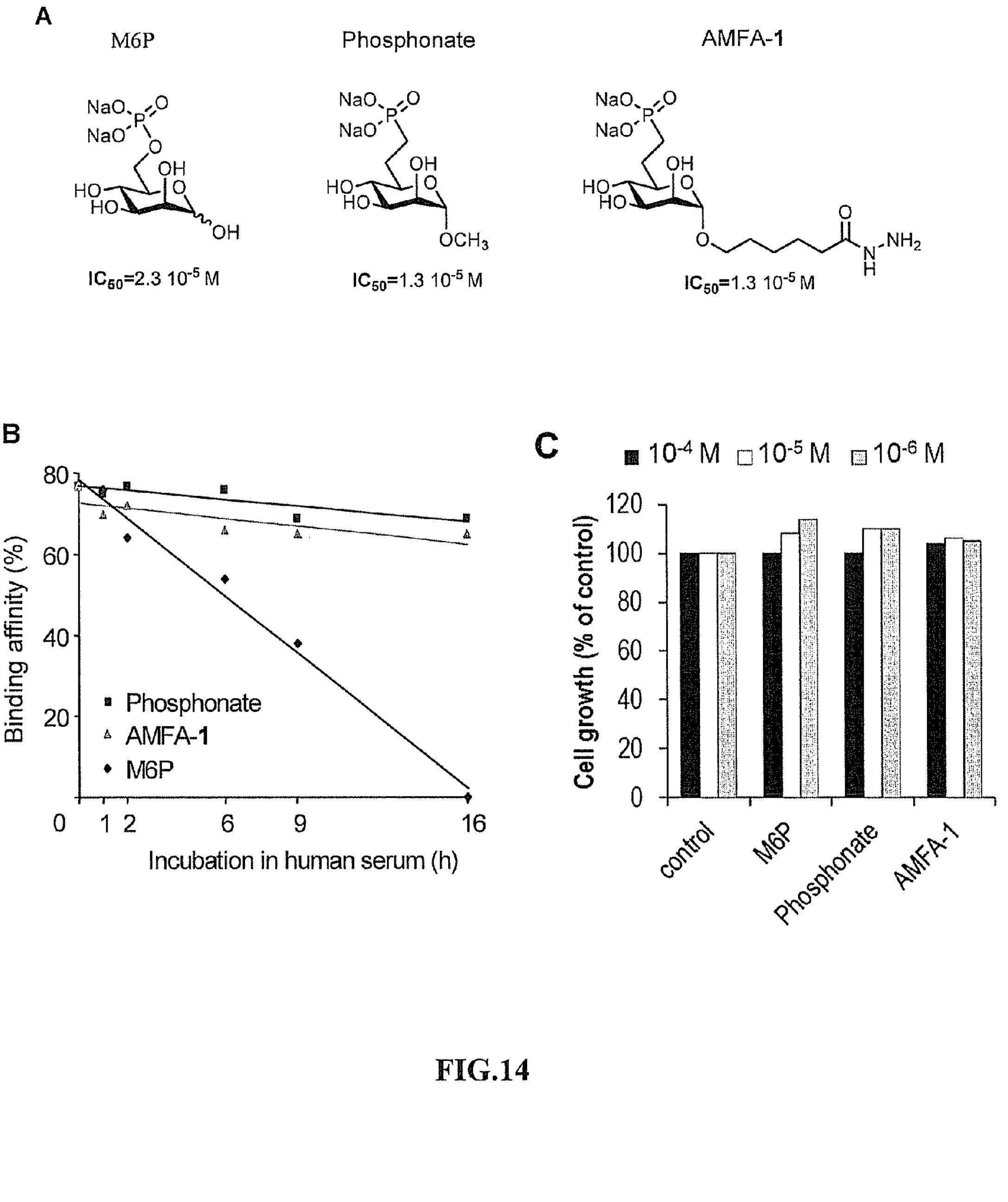
FIG. 14: Analysis of the pharmacological properties of AMFA-1. (A) IC50; (B) CI-M6PR binding affinity and stability in human serum, (C) toxicity in human fibroblasts.

As shown in FIG. 14, the binding affinity, the stability in 75% (v/v) human serum and the absence of toxicity in human fibroblasts of AMFA-1 were identical to those of phosphonate 1 alone. Similarly, AMFA-1 showed no toxicity in human breast cancer cell lines, MCF7 and MDA (data not shown). This indicates that the hexanehydrazide linker addition in anomeric position does not alter the pharmacological properties of the M6P-analogue.

Figure 15:
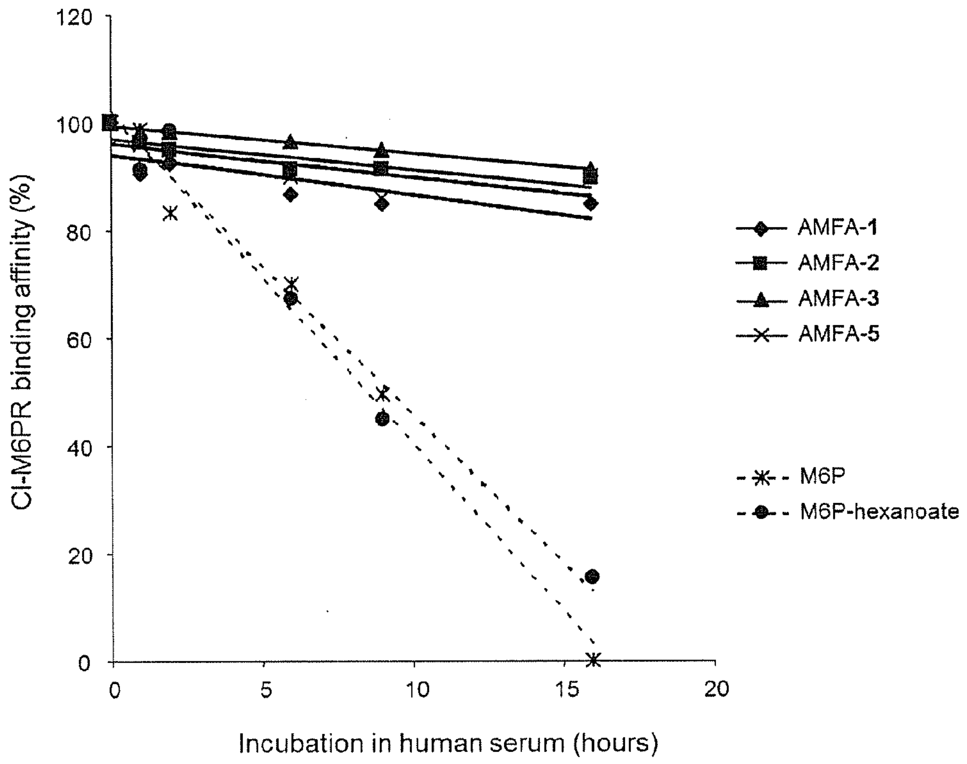
FIG. 15: Analysis of the pharmacological properties of AMFA-1, AMFA-2, AMFA-3, AMFA-5 in comparison with M6P and M6P-hexanehydrazide: CI-M6PR binding affinity at 20° C. (A) and in human serum (B).

1.9. Pharmacological Properties Analysis of AMFA-1, AMFA-2, AMFA-3, AMFA-5, M6P and M6P-Hexanehydrazide The binding affinity of AMFA-1, AMFA-2, AMFA-3 and AMFA-5 to CI-M6PR was determined at 20° C. (A) or in the presence of 75% human serum at 37° C. (B) and compared to M6P and M6P-hexanehydrazide. Methods are identical to 1.8 section. AMFA-1, AMFA-2, AMFA-3 and AMFA-5 shows a high potential to target CI-M6PR since they bind CI-M6PR with high binding affinity and are stable under blood incubation (FIG. 15). M6P-hexanehydrazide and M6P displayed a stable affinity in buffer solution but were hydrolysed in human serum with decrease of their affinity of ~50% after 7-8 h and of 84 and 100% after 16 h, respectively. AMFA-1, AMFA-2, AMFA-3 and AMFA-5 appear to retain a binding capacity superior to 85% after 16 h incubation in human serum. This indicates that a higher stability in serum and CI-M6PR affinity is only obtained with some M6P analogues.

1.10. Synthesis of cathD-AMFA-1 (a Conjugate According to the Invention)

An example of AMFA-1 coupling was performed on a human lysosomal enzyme, the cathepsin D. A cathepsin D-KDEL mutant was obtained by adding a C-terminal KDEL extension (for endoplasmic reticulum retention) by cDNA directed-mutagenesis and was then purified after stable expression in rat cancer cells [Liaudet E. et al., *Oncogene* 9: 1145-54, 1994]. In fact, the KDEL signal partially prevents the addition of the M6P signal in Golgi apparatus. This protein was used as a model being its oligomannosidic chains similar to those produced by baculovirus/insect cell system [Liaudet E. et al., *Oncogene* 9: 1145-54, 1994].

In order to realize the coupling between the AMFA and the lysosomal enzymes, we have developed an experimental protocol:

First, the phosphonate analogue-1 is functionalized at the anomeric position by a hexanehydrazide spacer arm containing a hydrazide group in order to obtain the AMFA-1.

Second, to perform the grafting, 0.5 mg/ml of human recombinant enzyme (here cathD-KDEL) and 10 mM sodium meta-periodate solution ($NaIO_4$) are reacted in a 0.1 M sodium acetate buffer pH 5.5 for 30 min at 4° C. in the dark. Glycerol (15 mM final concentration) is added for 5 min at 0° C. to stop the reaction and the sample is dialysed overnight against 0.1 M sodium acetate buffer pH 5.5.

Third, AMFA-1 is added and let react under agitation for 2 h at room temperature. Finally, samples are dialysed overnight against PBS buffer. This protocol can be easily adapted for grafting human recombinant enzymes coming from baculovirus to high potent AMFA. Since, the number of glycosylated chains in various lysosomal enzymes is different, the protein/AMFA relative ratios and the reaction conditions (time, t°, pH) should be optimized for each enzyme to reach high CI-M6PR affinity and activity of the neoglycoenzymes.

This kind of reaction induces the oxidization of oligomannosidic moiety and permits to obtain aldehyde functions that react with the hydrazide function of the AMFA-1 in a covalent manner to form classical acylhydrazone functions. Hydrazides selectively react with aldehyde to form acylhydrazone through traceless conjugation conditions, since no side products or potentially toxic reagents are involved. Similarly, aminoxy groups (cf AMFA-3) react with aldehydes to form oxime functions. Moreover, only the oligomannosidic moiety is remodeled and the peptidic moiety of the enzyme is not affected by the conditions used for grafting AMFA.

Here, enzymes are grafted to AMFA via acylhydrazone or oxime bonds.

1.11. Binding Assay and Catalytic Activity of cathD-AMFA-1

The binding assays of the cathD-AMFA-1 were performed using biotinylated CI-M6PR to the same protocol used for AMFA-1 binding assay, as detailed in section 1.2.

Figure 16:
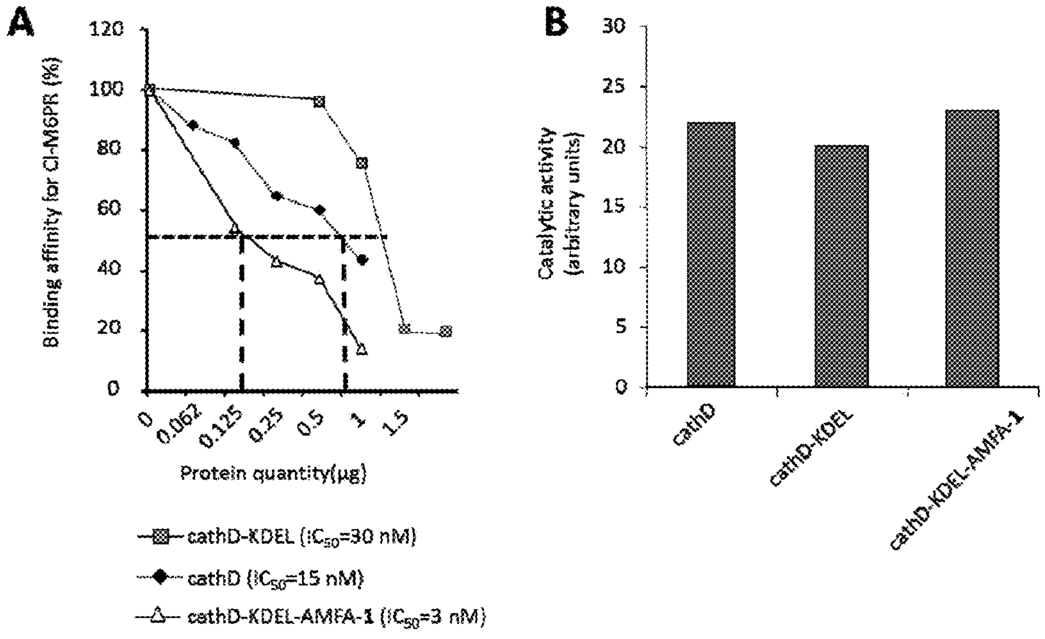
FIG. 16: Effect of AMFA-1 grafting on oligomannosidic chains of a human recombinant enzyme. (A) binding affinity; (B) catalytic activity.

The affinity for CI-M6PR of AMFA-1-modified cathepsin D-KDEL (Kd=3 nM) is 10-fold higher than the one of native cathepsin D-KDEL (Kd=30 nM) (FIG. 16A). Interestingly, its affinity is 5-fold increased compared to that of natural cathepsin D (Kd=15 nM) which is a high affinity ligand for CI-M6PR, due to the presence of bisphosphorylated chains able to occupy the two M6P binding sites of the receptor. These data indicate that the affinity of AMFA-1 conjugated chains is very close to that of bisphosphorylated chains (Kd=2 nM) which are the natural chains displaying the highest affinity for the CI-M6PR [Tong P Y et al., *J Biol. Chem.* 264, 7962-9, 1989].

At the same time, the catalytic activities of natural cathepsin D, cathepsin D-KDEL and cathepsin D-KDEL grafted on AMFA-1 were measured using the quenched fluorescent substrate Edans-Arg-Pro-Ile-Leu-Phe-Phe-Arg-Leu-Gln-Dabcyl synthesized by the UMR 5247 (FIG. 16B). After proteolytic cleavage of the peptide backbone, released Edans regains its fluorescent properties under light excitation (exc. 355 nm; em. 538 nm). The activity of cathepsin D-KDEL was found totally maintained after AMFA-1 coupling, indicating that the carbohydrate remodelling reaction does not affect the structure of its catalytic site.

We have thus defined a reproducible protocol for the obtaining of neoglycoenzymes with a high affinity for CI-M6PR and a maintained catalytic activity.

1.12 In Vivo Targeting of Iduronidase-AMFA-1 in Fibroblasts of Patients with Scheie or Hurler Lysosomal Disorder and Activity on Glycosaminoglycan Secretion The enzyme selected for this study is the α-L-iduronidase (IDUA) [EC 3.2.1.76] involved in the mucopolysaccharidosis I (MPSI), a mucopolysaccharide storage disorder (Neufeld, E. F. and Muenzer, J. 1995, *In The metabolic basis of inherited disease*, Scriver, C. R., Beaudet, A. L., Sly, W. S., and Valle, D., eds., 7th ed. New York: McGraw-Hill, pp. 2465-2494). A reduced or absent IDUA activity results in the accumulation of the enzyme substrate, the glycosaminoglycans (GAG), in different tissues. MPSI is a multi-organ disorder and may affect appearance, mental development, and mobility and its clinical manifestations vary from the mildest form, i.e. Scheie's, to the most severe one, Hurler's (Kakkis, *N Engl J Med* 2001, 344, 3:182-188). Prevalence in Europe is about 0.025 in 10,000 persons.

IDUA is a 653 AA protein, glycosylated with six N-linked oligosaccharides to produce a 74-kDa precursor molecule, and that is processed into a mature form.

Figure 17:
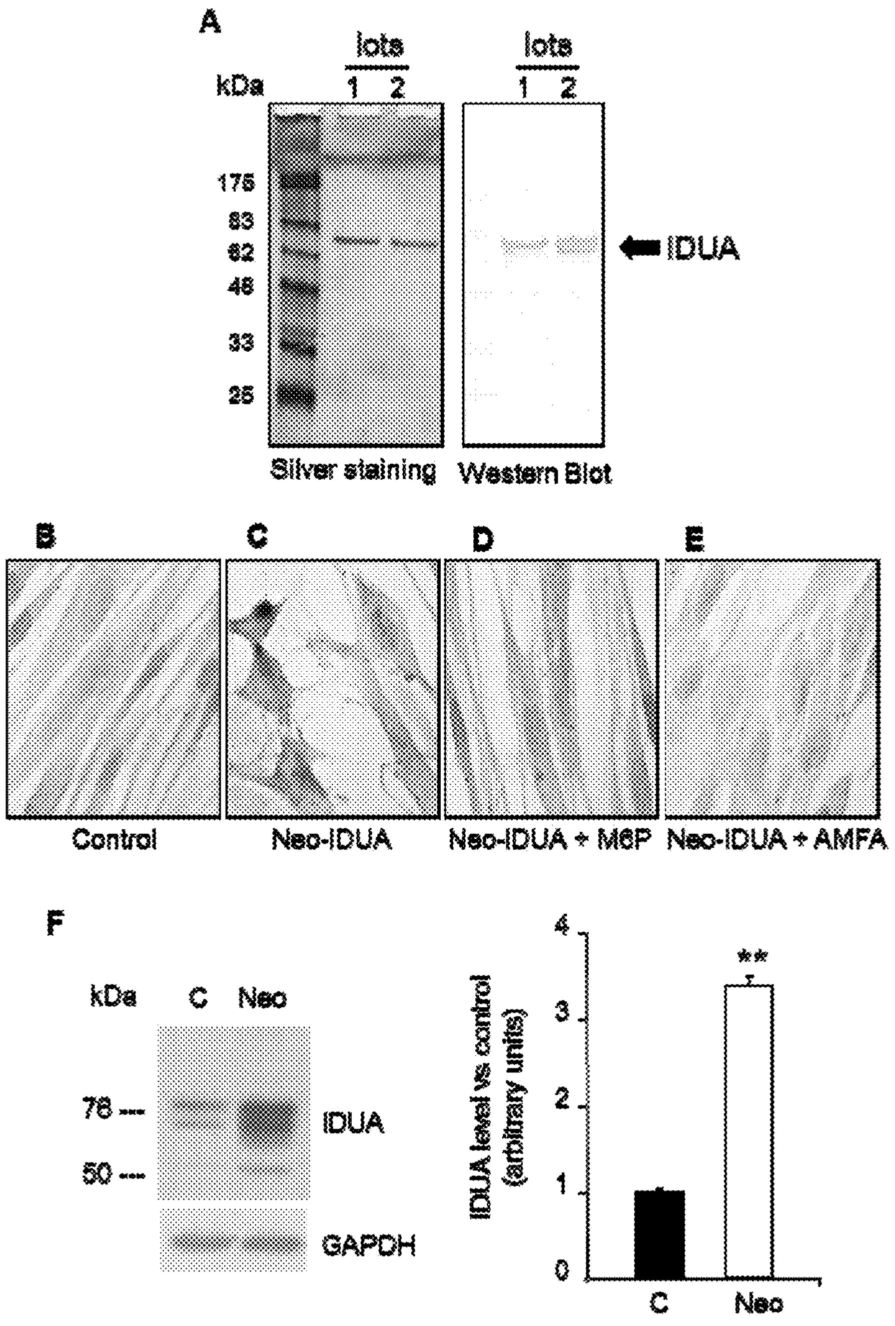
FIG. 17: Iduronidase (IDUA) purification (A), immunohistochemical uptake detection of neo-IDUA (B-E) and SDS polyacrylamide gel detection of intracellular neo-IDUA (F) in Scheie and Hurler fibroblasts.

The production and purification of the enzyme IDUA was performed in the baculovirus/lepidopteran cell expression system. Briefly, a Flag sequence (Asp-Tyr-Lys-Asp-Asp-Asp-Asp-Lys) was introduced at the N-terminus of the IDUA c-DNA and these sequences had been inserted in specific baculovirus transfer vector, downstream of the very late P10 promoter. Recombinant viruses are generated by cotransfecting Sf9 cells with purified viral DNA and the transfer vector bearing the enzyme c-DNA. Thereafter, baculoviruses are cloned by plaque assays. Ten isolated viral clones are amplified and the expression of the protein is controlled by ELISA and western blotting using an anti-FLAG antibody. After the selection of one clone for the enzyme production, Sf9 cells have been infected with the selected recombinant virus at a multiplicity of infection of 2 PFU (plaque Forming Unit)/cell. After four days incubation at 28° C., supernatants have been collected, diafiltrated and deposed on a concanavalin A affinity column (ConA Sepharose, GE Healthcare). Proteins are eluted with α-methyl mannose. Subsequently, the recombinant IDUA has been purified (i) by His-select Nickel affinity chromatography (Sigma) and eluted with His-select elution buffer (Sigma, imidazole 250 mM). Once eluted, the enzyme has been dialysed with 100 mM NaCl, 100 mM acetate buffer pH 5.8. The neoIDUA was analyzed by SDS polyacrylamide gels and its purity determined by silver staining (FIG. 17 A). The identification of the enzyme was obtained by Western blotting using specific monoclonal anti-IDUA antibodies (R&D Systems).

After being coupled to AMFA-1 as described in 1.10 section, neoIDUA cell internalisation, toxicity and substrate reduction were evaluated in MPSI fibroblasts.

As observed at light microscopy, 100 ng/mL neoIDUA was already internalised by MPSI fibroblasts from Scheie patient after 3 h incubation (FIG. 17 B-E). The uptake of neoIDUA by the cells was strongly decreased by pre-incubation with 10 mM M6P (FIG. 17D), and totally prevented by 10 mM AMFA-1 (FIG. 17E). These data demonstrate that neoIDUA uptake involves CI-M6PR. Moreover the internalization of neoIDUA was also demonstrated by Western Blot in cell extracts after 24 h incubation (FIG. 17F). Glyceraldehyde 3-phosphate dehydrogenase (GAPDH) immunodetection was used as an internal control for total protein loading.

By measuring the levels of the enzymatic substrate (GAG) by Blyscan kit (Tebu-Bio) secreted in the culture medium of Hurler patient fibroblasts, neoIDUA was observed to significantly reduce up to 50% GAG secretion from 24 to 72 h (Table 1). This demonstrates that neoIDUA was still active up to 72 h in cells.

TABLE 1

Secreted GAG concentrations in culture medium from Hurler patient fibroblasts (μg/ml)

| Time treatment | Hurler patient fibroblasts (control) | Hurler patient fibroblasts + IDUA-AMFA-1 |
|---|---|---|
| 24 h | 0.018 | 0.009 |
| 48 h | 0.022 | 0.016 |
| 72 h | 0.032 | 0.018 |

Figure 18:
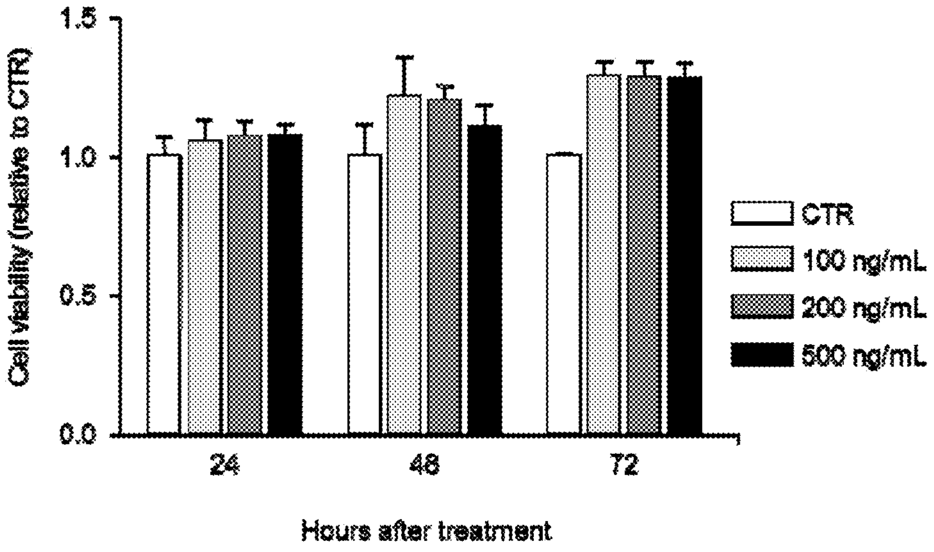
FIG. 18: Viability of Hurler fibroblasts treated at different doses of NeoIDUA.

As shown in FIG. 18, treatments of Hurler fibroblasts by 100-500 ng/mL neoIDUA were not toxic and slightly potentiate cell viability at 72 h. Cell viability was evaluated by MTT assay [Maynadier et al. *FASEB J*, 22: 671-81, 2008].

1.13. Therapeutic Efficacy of IDUA AMFA-1 in Mucopolysaccharidosis I (MPSI) Mouse Model Homozygous IDUA −/− mice (6-8 week-old) were treated intravenously with vehicle alone (control) or with 0.16 mg neoIDUA/kg body weight/week for 6 weeks. The secreted GAG were assayed in urine after 6 injections and normalized to urine creatinine concentrations using methods previously described [Barbosa et al., *Glycobiology Adv. Access* 13: 647-53, 2003].

The secreted GAG concentrations were significantly decreased in urine to 59.8% by this treatment (see Table 2). This indicates the efficacy of IDUA-AMFA-1 for MPS-I therapy. This data indicate the therapeutic efficacy of IDUA-AMFA-1 enzyme obtained by a production in the baculovirus expression system and the subsequent AMFA grafting for CI-M6PR targeting.

TABLE 2

Secreted GAG concentrations/creatinine concentrations in urine of MPS-I homozygous mice (% control).

| Time treatment | Control MPS-I mice (5 mice) | MPS-I mice + IDUA-AMFA-1 (0.16 mg/kg body weight) (6 mice) |
|---|---|---|
| 6 weeks | 100 ± 18.5 | 59.8 ± 9.0* |

Mean ± SD;
*$p < 0.0005$ (Student's t test).

The invention claimed is:

1. A conjugate, wherein said conjugate is a product of interest Y selected from the group consisting of glycoproteins, nanoparticles and labels for medical imaging, conjugated via a linker L with a compound having the formula (1)

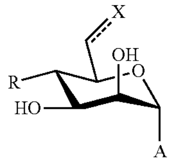

(1)

wherein the dotted line represents a bond which is present or not,

X represents an analogue of a phosphate group,

R is selected from the group consisting of H and OH,

A is selected from the group consisting of O, S and $CH_2$, and wherein said compound having the formula (1) is linked to the linker via the A moiety, said linker L separates A and Y by a chain of 4 to 15 consecutive atoms, when said bond represented by the dotted line is not present, X is selected from the group consisting of:

a saturated phosphonate group having the formula

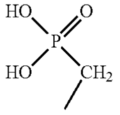

($X_1$), a bis-fluoro phosphonate group having the formula

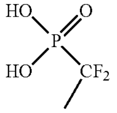

($X_2$), a fluoro phosphonate group having the formula

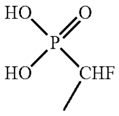

($X_3$), a saturated carboxylate group having the formula

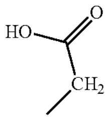

($X_4$), a malonate group having the formula

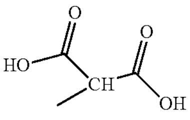

($X_5$), when said bond represented by the dotted line is present, X is selected from the group consisting of:

an unsaturated phosphonate group having the formula

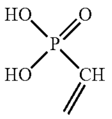

($X_6$), and an unsaturated carboxylate group having the formula

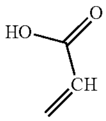

($X_7$).

2. The conjugate according to claim 1, wherein said conjugate has an $IC_{50}$ for the cation-independent mannose 6-phosphate receptor (CI-M6PR) of at most 100 μM.

3. The conjugate according to claim 1, wherein Y is conjugated via a linker L with at least 1, 2, 3, 4, 5, 6, 7, 8, 9, 10, 100, 1000 or more compounds having the formula (1).

4. The conjugate according to claim 1, wherein said conjugate is a product of interest Y conjugated via a linker L with at least two compounds having the formula (1), wherein two analogues of mannose 6-phosphate of said at least two compounds are recognizable by the two mannose 6-phosphate binding sites of a same cation-independent mannose 6-phosphate receptor (CI-M6PR1, or by two mannose 6-phosphate binding sites of a CI-M6PR dimer.

5. The conjugate according to claim 1, wherein Y is a lysosomal enzyme.

6. The conjugate according to claim 4, wherein said conjugate has an $IC_{50}$ for the cation-independent mannose 6-phosphate receptor of at most 100 nM.

7. The conjugate according to claim 1, wherein said chain of atoms of said linker L is a substituted or not, linear or branched $C_1$-$C_{30}$ alkyl or alkenyl chain, wherein one or more carbon atom of said chain are optionally replaced by a chemical group selected from the group consisting of ether (—O—), amine (—NH), thioether (—S—), amide (—CO—NH—), urea (—NH—CO—NH—), carbamate (—NH—CO—O—), and cyclic or heterocyclic systems, said cyclic or heterocyclic systems being saturated or not and substituted or not, provided that said chain separates the A and the Y moieties by 4 to 15 consecutive atoms.

8. The conjugate according to claim 1, wherein said linker L is selected from the group comprising:

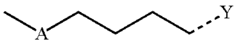
($L_1$);

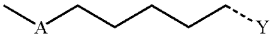
($L_2$);

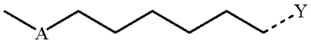
($L_3$);

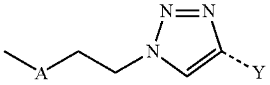
($L_4$);

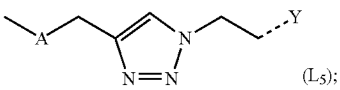
($L_5$); and

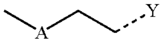
($L_6$)

wherein

"-----Y" represents either:

(a) —Y, or (b) -T-Y, wherein T is part of the linker and represents a chemical moiety selected from the group consisting of

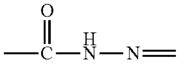
and —O—N═;

and

"A-" represents the remainder of the compound according to the invention as defined in formula (1).

9. The conjugate according to claim 6, wherein said conjugate has an $IC_{50}$ for the cation-independent mannose 6-phosphate receptor of at most 50 nM.

10. The conjugate according to claim 6, wherein said conjugate has an $IC_{50}$ for the cation-independent mannose 6-phosphate receptor of at most 25 nM.

11. The conjugate according to claim 6, wherein said conjugate has an $IC_{50}$ for the cation-independent mannose 6-phosphate receptor of at most 2 nM.

12. A method for treating a lysosomal storage disorder in a human or animal body in need thereof comprising administering to said human or animal body a therapeutically effective amount of the conjugate according to claim 1, wherein Y is a lysosomal enzyme missing or deficient in said lysosomal storage disorder.

13. The method for treating a lysosomal storage disorder in a human or animal body according to claim 12, wherein said lysosomal storage disorder is muccopolysaccharidosis type 1.

14. The method for treating a lysosomal storage disorder in a human or animal body according to claim 13, wherein said the compound of formula (1) of the conjugate is selected from the group consisting of 5-hydrazinocarbonylpentyl 6-deoxy-6-dihydroxyphosphinylmethyl-α-D-mannopyranoside, (hydrazinocarbonylethyl)-1H-1,2,3-triazol-4-yl-methyl 6-deoxy-6-dihydroxyphosphinylmethylene-α-D-mannopyranoside, 2-(aminoxy)ethyl 6-deoxy-6-dihydroxyphosphinylmethylene-α-D-mannopyranoside and [5-methoxycarbonylpentyl 6,7-dideoxy-7-(carboxy)-α-D-manno-octopyranoside]uronate.

15. The method for treating a lysosomal storage disorder in a human or animal body according to claim 13, wherein the conjugate administered to the patient is iduronidase grafted to 5-hydrazinocarbonylpentyl 6-deoxy-6-dihydroxyphosphinylmethyl-α-D-mannopyranoside.

16. The method for treating a lysosomal storage disorder in a human or animal body according to claim 12, wherein the compound of formula (1) of the conjugate is selected from the group consisting of 5-hydrazinocarbonylpentyl 6-deoxy-6-dihydroxyphosphinylmethyl-α-D-mannopyranoside, (hydrazinocarbonylethyl)-1H-1,2,3-triazol-4-yl-methyl 6-deoxy-6-dihydroxyphosphinylmethylene-α-D-mannopyranoside, 2-(aminoxy)ethyl 6-deoxy-6-dihydroxyphosphinylmethylene-α-D-mannopyranoside and [5-methoxycarbonylpentyl 6,7-dideoxy-7-(carboxy)-α-D-manno-octopyranoside]uronate.

17. A compound having the formula (I)

(I)

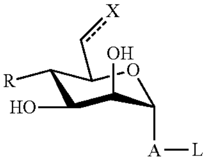

wherein the dotted line represents a bond which is present or not,

X represents an analogue of a phosphate group,

R is selected from the group consisting of H and OH,

A is selected from the group consisting of O, S and $CH_2$,

L represents a linker comprising a terminal chemically reactive group Z capable of reacting with a product of interest Y to form a conjugate wherein the A and the Y moieties are separated by 4 to 15 consecutive atoms, and wherein:

when said bond represented by the dotted line is not present, X is selected from the group consisting of:

a saturated phosphonate group having the formula ($X_1$)

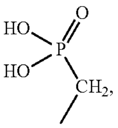

a bis-fluoro phosphonate group having the formula (X2)

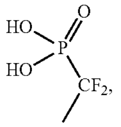

a fluoro phosphonate group having the formula (X3)

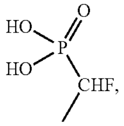

a saturated carboxylate group having the formula (X4)

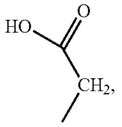

and a malonate group having the formula (X5)

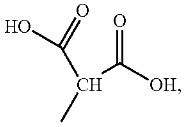

when said bond represented by the dotted line is present, X is selected from the group consisting of:

an unsaturated phosphonate group having the formula (X6)

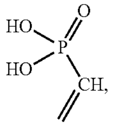

and an unsaturated carboxylate group having the formula (X7)

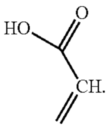

18. A method for producing a conjugate, said method comprising the step of reacting a product of interest Y selected from the group consisting of glycoproteins, nanoparticles and labels for medical imaging, with a compound having the formula (I)

(I)

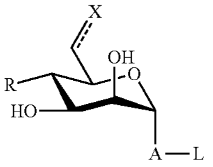

wherein the dotted line represents a bond which is present or not,

X represents an analogue of a phosphate group,

R is selected from the group consisting of H and OH,

A is selected from the group consisting of O, S and $CH_2$,

L represents a linker comprising a terminal chemically reactive group Z capable of reacting with the product of interest Y to form said conjugate wherein the A and the Y moieties are separated by 4 to 15 consecutive atoms, and wherein when said bond represented by the dotted line is not present, X is selected from the group consisting of:

a saturated phosphonate group having the formula ($X_1$)

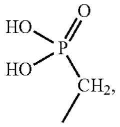

a bis-fluoro phosphonate group having the formula ($X_2$)

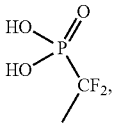

a fluoro phosphonate group having the formula ($X_3$)

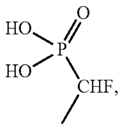

a saturated carboxylate group having the formula
(X4)
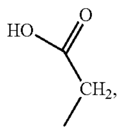
and
a malonate group having the formula
(X5)
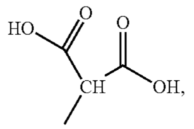
when said bond represented by the dotted line is present, X is selected from the group consisting of:
an unsaturated phosphonate group having the formula
(X6)
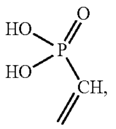
and
an unsaturated carboxylate group having the formula
(X7)
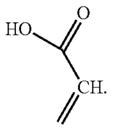
* * * * *